United States Patent [19]

Goodey et al.

[11] Patent Number: 5,667,986
[45] Date of Patent: Sep. 16, 1997

[54] YEAST PROMOTER FOR EXPRESSING HETEROLOGOUS POLYPEPTIDES

[75] Inventors: Andrew R. Goodey; Darrell Sleep, both of Nottingham; Dina Vakeria, London, all of England

[73] Assignee: Delta Biotechnology Limited, Nottingham, United Kingdom

[21] Appl. No.: 270,076

[22] Filed: Jul. 1, 1994

Related U.S. Application Data

[63] Continuation-in-part of Ser. No. 925,286, Aug. 4, 1992, abandoned, which is a continuation of Ser. No. 597,687, Oct. 16, 1990, abandoned.

[30] Foreign Application Priority Data

Oct. 18, 1989 [GB] United Kingdom ............... 8923521

[51] Int. Cl.⁶ ............................ C12P 21/06; C12N 1/19; C12N 15/11; C12N 15/63
[52] U.S. Cl. .............. 435/69.1; 435/254.2; 435/320.1; 536/24.1
[58] Field of Search ............... 435/69.1, 172.1, 435/254.2, 172.3, 252.3, 320.1, 254.11; 536/23.1, 24.1

[56] References Cited

U.S. PATENT DOCUMENTS 4,751,180  6/1988  Cousens et al. ................ 435/69.7

*Primary Examiner*—Mindy Fleisher
*Assistant Examiner*—Terry A. McKelvey
*Attorney, Agent, or Firm*—Steven J. Moore

[57] ABSTRACT

A yeast promoter comprising the promoter of the (cytoplasmically located glycerol-3-phosphate dehydrogenase gene (GPD 1) possesses advantageous capacity to regulate the expression of heterologous polypeptides in yeasts transformed therewith. Expression of such polypeptides utilizing the GPD1 promoter can be regulated by the presence(repressed) or absence(derepressed) of high levels of sucrose or glucose in the fermentation medium. Alternatively, a non-repressing carbon source, such as glycerol or ethanol, can be added to the fermentation medium.

12 Claims, 8 Drawing Sheets

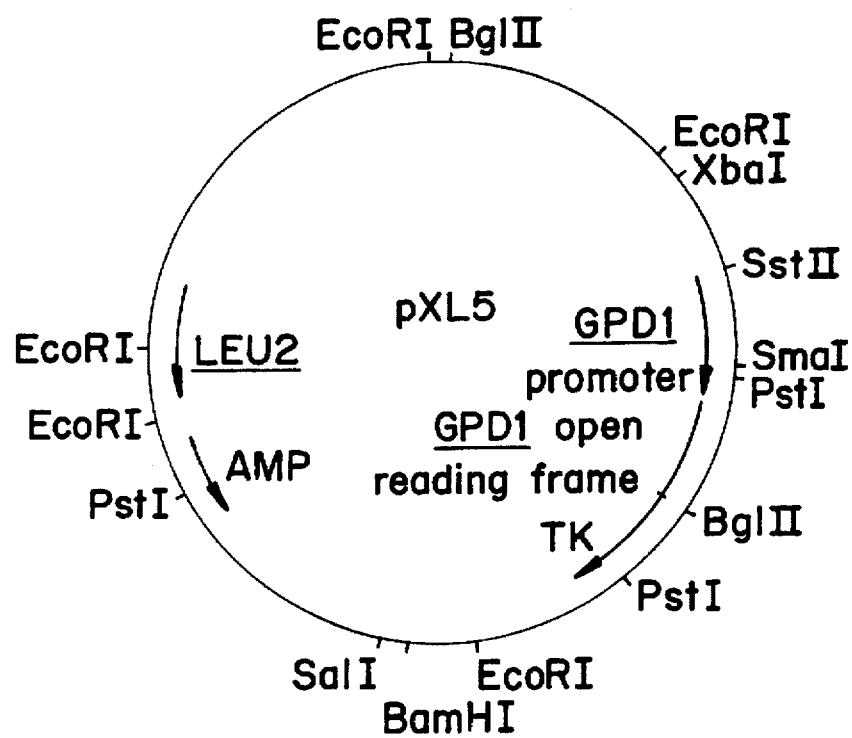
FIG_1
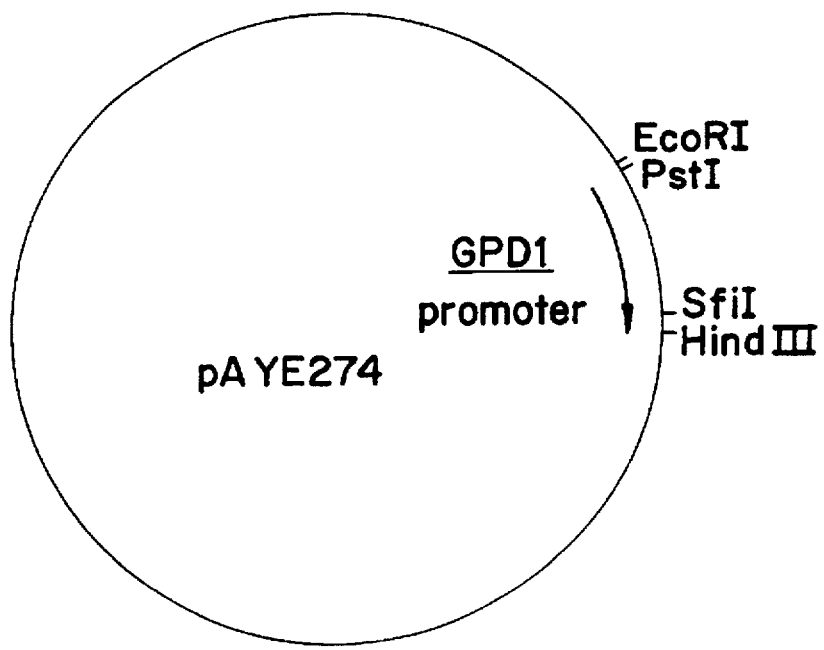
FIG_2

FIG_10
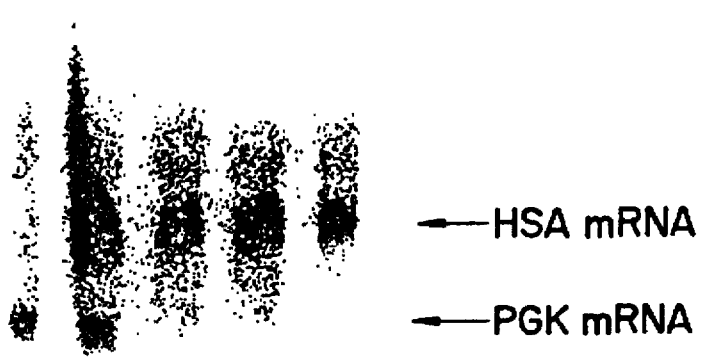
FIG_11
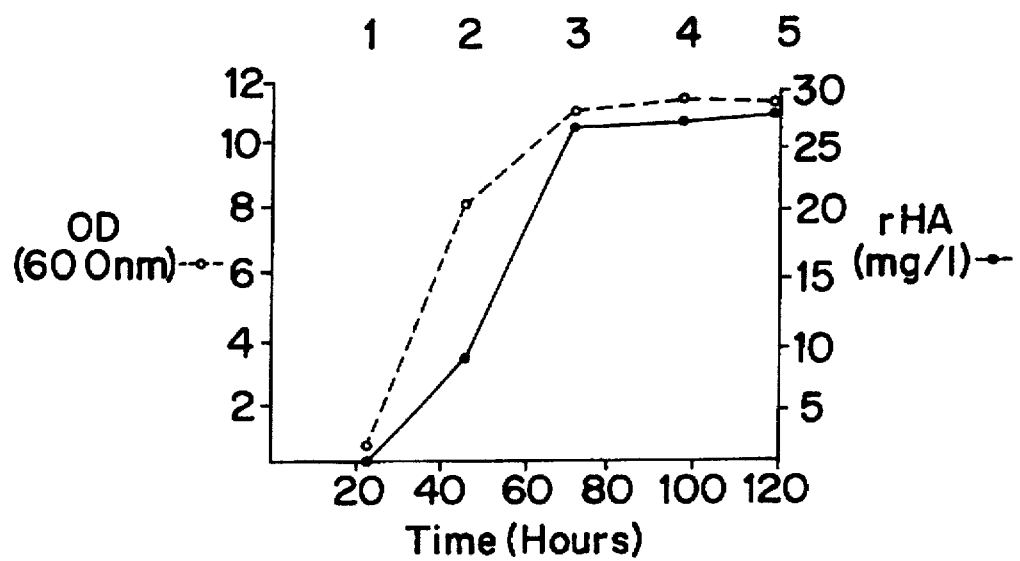

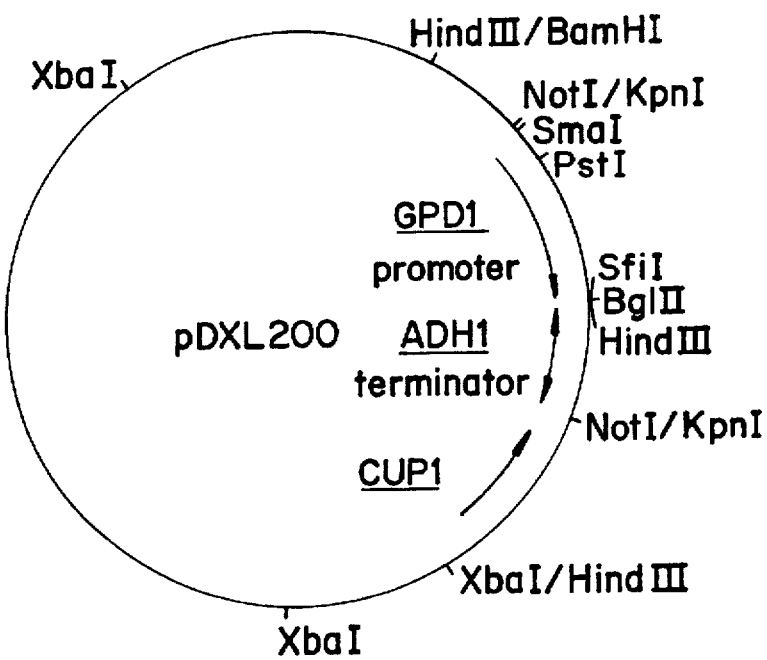
FIG_12
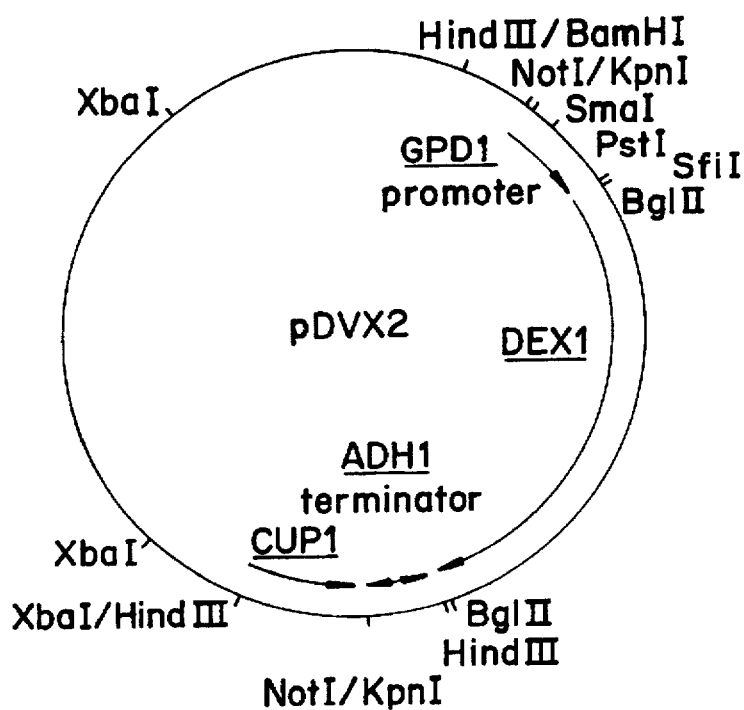
FIG_13

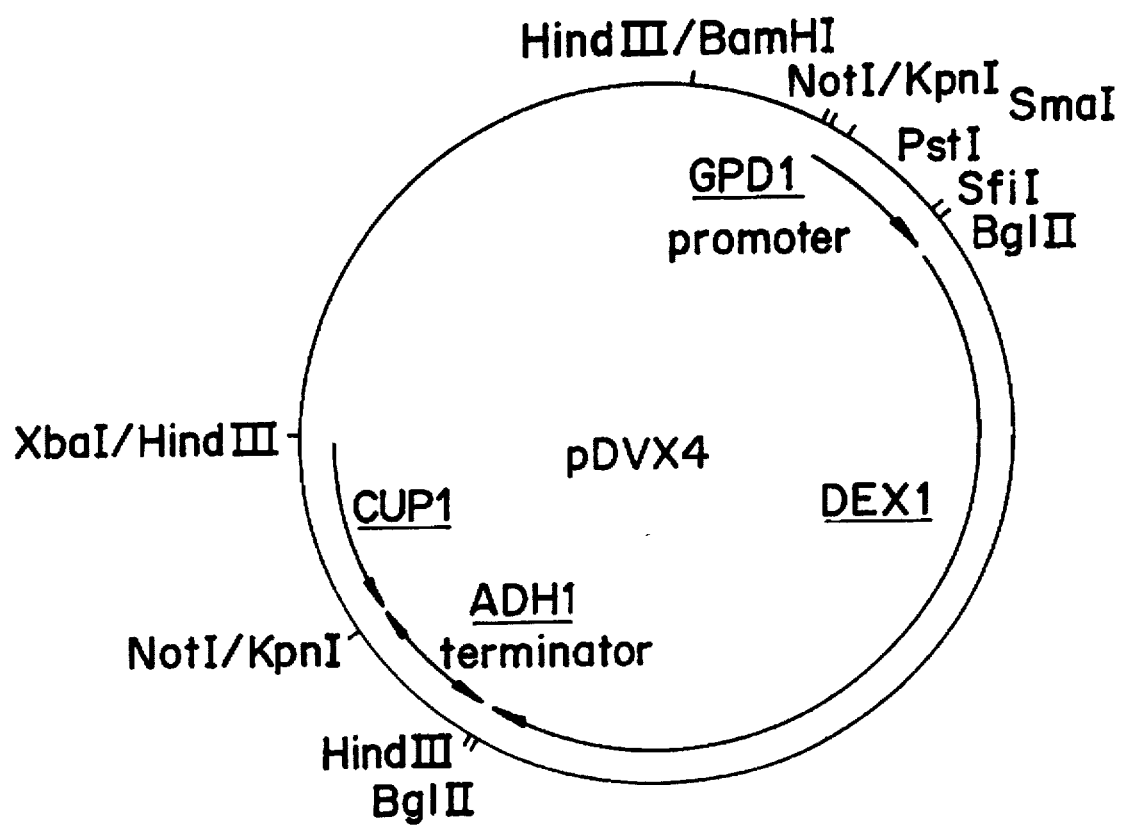
FIG_14

YEAST PROMOTER FOR EXPRESSING HETEROLOGOUS POLYPEPTIDES

RELATED APPLICATIONS

This application is a continuation-in-part of U.S. patent application Ser. No. 07/925,286 filed Aug. 4, 1992 now abandoned, which is, a continuation of U.S. patent application Ser. No. 07/597,687, filed Oct. 16, 1990, now abandoned.

The present invention relates to yeast promoters which will direct expresion of coding sequences in yeasts, such as *Saccharomyces cerevisiae*.

BACKGROUND OF THE INVENTION

Nucleotide sequences isolated from yeasts which have been shown to be useful for directing the expression of heterologous coding sequences are known in the art as promoters. Those skilled in the art recognize that the term "heterologous", means that the coding sequence is not the one whose expression is directed by the promoter in the wild-type organism in which the promoter is found. In most instances, the coding sequence is one which is not found in the wild-type organism at all.

The construction of cloning vectors or expression vectors containing such promoters and the incorporation thereof into plasmids that are in turn utilized to transform yeasts are likewise known in the art. Those skilled in the art are likewise aware that such transformants can be utilized in fermentation processes to express desired polypeptides coded for by the heterologous polynucleotides in the vectors.

There is an ongoing quest for such promoters that have improved efficiency and the capacity to be regulated for use in large scale fermentation operation to produce desired polypeptides. Such an advantageous promoter has been found in accordance with the present invention.

SUMMARY OF THE INVENTION

The invention provides a novel DNA promoter sequence, or a variant or functional portion thereof, a cloning vector or yeast expression vector comprising the promoter adjacent a restriction site such that a heterologous coding sequence may be located downstream of the promoter, hybrid vectors having one or more DNA inserts each comprising the promoter, hosts transformed therewith and process of utilizing such hosts to prepare desired polypeptides.

BRIEF DESCRIPTION OF THE DRAWINGS

FIGS. 1 to 9 are respective restriction maps of plasmids pXL5, pAYE274, pAYE275, pAYE334, pAYE276, pAYE323, pAYE324, pSAC35 and pAYE321;

FIG. 10 is a photograph of a gel showing labelled RNA from a cell culture at differing times;

FIG. 11 is a graph showing the time course of expression of the glycerol-3-phosphate dehydrogenase promoter corresponding to FIG. 10;

FIG. 12 is a restriction map of plasmid pDXL200;

FIG. 13 is a restriction map of plasmid pDVX2; and

FIG. 14 is a restriction map of plasmid pDVX4.

DETAILED DESCRIPTION OF THE INVENTION

Figure 3:
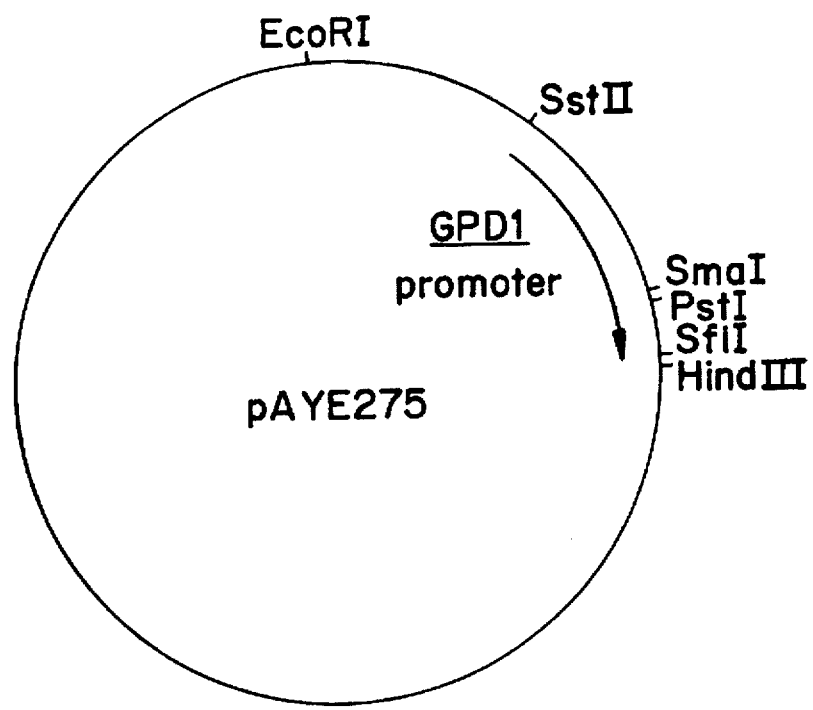

In accordance with the present invention, there is provided a DNA promoter sequence SEQ ID NO: 1, or a variant or a functional portion of said sequence, in isolation from the coding sequence which would normally neighbor the said sequence in wild-type *Saccharomyces cerevisiae*.

Although it will usually be undesirable, because a fusion protein will be produced when the promoter is used to express a heterologous protein, the promoter of the invention may be accompanied by a portion of the coding sequence which normally abuts it.

The variants or functional portions of the promoter sequence of the invention are characterized by having minor variations of nucleotides and/or a shorter length, respectively, but which still retain at least 10% (preferably 80%, 90%, 95% or 99%) of the transcription rate capacity of the said sequence to promote transcription of a heterologous polynucleotide positioned downstream thereof, with the other parameters of the two expression systems which are being compared (such as 3' regulatory regions) being the same. In the case of a portion of the said sequence, such regulatory activity may be determined for the portion alone (ie without any other 5' regulatory sequence) or in conjunction with another 5' regulatory sequence positioned 5' or 3' to the said portion. Preferably, a "variant" has 80%, 90%, 95%, or 99% sequence identity with the said promoter sequence.

Preferably, the functional portion of the subject promoter sequence has 80%, 90%, 95%, 99% or 100% sequence identity with that region of the promoter sequence most identical therewith. Preferably, the portion is at least 100 nucleotides long, more preferably at least 200, 300, 400, 500, 1000 or 1500 nucleotides long. Suitably, the "functional portion" retains the ability of the said sequence to be repressed in the presence of carbon catabolite-repressing energy sources such, as glucose and sucrose, and to be derepressed in the absence of such sources whether or not glycerol or ethanol are present.

Suitably, the 3' end of any functional portion of the subject promoter sequence corresponds to the 3' end of SEQ ID NO: 1 and the said portion extends continuously away from the said 3' end in a 5' direction for up to about 1.35 or 1.40 kbp, beyond which (in the native environment) there appears to be a gene for Ala-tRNA$^{GCU}$. In nature, the 3' end of SEQ ID NO: 1 immediately precedes the ATG start codon. Advantageously, the functional portion comprises SEQ ID NO: 3, in other words the 379 bp region immediately upstream of the ATG start codon, optionally with further 5' sections of the said sequence.

The promoter of this invention is the promoter for the *S. cerevisiae* cytoplasmically located NAD-linked glycerol-3-phosphate dehydrogenase gene (GPD1) as correctly identified by Larsson, K. et al., 1993, *Molecular Microbiology* 10, 1101–1111. This enzyme is one of two activities required to convert glycerol into dihydroxyacetone phosphate. These are essential enzymes if glycerol is supplied as a sole carbon source. *S. cerevisiae* possesses two distinct forms of glycerol-3-phosphate dehydrogenase encoded by distinct, unlinked genes; a mitochondrially located FAD-linked enzyme encoded by the GUT2 gene (Rønnow, B. and Kielland-Brandt, M. C., 1993, Yeast 9, 1121–1130), and a cytoplasmically located NAD-linked enzyme encoded by the GPD1 gene, the promoter of which is the subject of the present invention. SEQ ID NO: 2 shows a part of the 5' region flanking the promoter of GPD1, and is constituted by the SEQ ID NO: 1 region plus 123 bp upstream thereof, and the ATG start codon.

A promoter of the invention may be located on a cloning vector or an expression vector adjacent a restriction site such that a heterologous polynucleotide may be located downstream of the promoter and in correct reading frame in relation to a translational start codon. The start codon may be provided on the vector (eg immediately 3' to the promoter) or it may be inserted as a 5' end of the heterologous polynucleotide. A linker may be provided between the promoter of the invention and the start codon, if desired. 3' Regulatory regions may similarly be provided on the vector or inserted with the heterologous polynucleotide. The transcription termination signal is preferably the 3' flanking sequence of a eukaryotic gene which contains proper signals for transcription termination and polyadenylation in fungi. Suitable 3' flanking sequences may, for example, be those of the glycerol-3-phosphate dehydrogenase gene or they may be different. Preferably, the termination signal is that of the S. cerevisiae PGK1 or ADH1 genes. Preferably, the DNA construct according to the present invention is provided at both ends with synthetic oligonucleotide linkers which allow insertion and cloning of the construct in a cloning vector. The promoter of the invention, the DNA coding sequence and the fungal transcription termination signals are operably linked to each other, ie they are juxtaposed in such a manner that their normal functions are maintained. Thus, the array is such that the expression control sequence effects proper expression of the heterologous polynucleotide and the transcription termination signals effect proper termination of transcription and polyadenylation. The junction of these sequences is preferably effected by means of synthetic oligonucleotide linkers which may carry the recognition sequence of an endonuclease.

According to the present invention there is further provided a hybrid vector having one or multiple DNA inserts each comprising a promoter of the invention, a DNA segment consisting of a DNA sequence coding for a desired polypeptide which DNA segment is under transcriptional control of said promoter, and a DNA sequence containing eukaryotic transcription termination signals. The hybrid vectors according to the invention are hybrid plasmids or linear DNA vectors and are selected depending on the host organism envisaged for transformation.

The invention relates also especially to hybrid plasmids which, apart from the expression control sequence, the above DNA segment and the sequence containing transcription termination signals, contain additional DNA sequences which are inessential or less important for the function of the promoter, ie for the expression of the desired polypeptide, but which perform important functions, for example in the propagation of the cells transformed with the hybrid plasmids. The additional DNA sequences may be derived from prokaryotic and/or eukaryotic cells and may include chromosomal and/or extra-chromosomal DNA sequences. For example, the additional DNA sequences may stem from (or consist of) plasmid DNA, such as bacterial or eukaryotic plasmid DNA, viral DNA and/or chromosomal DNA, such as bacterial, yeast or higher eukaryotic chromosomal DNA. Preferred hybrid plasmids contain additional DNA sequences derived from bacterial plasmids, especially Escherichia coli plasmid pBR322 or related plasmids, bacteriophage, yeast 2µ plasmid, and/or yeast chromosomal DNA.

In the preferred hybrid plasmids according to the invention, the additional DNA sequences carry a yeast replication origin and a selective genetic marker for yeast. Hybrid plasmids containing a yeast replication origin, eg an autonomously replicating segment (ars), are extrachromosomally maintained within the yeast cells after transformation and are autonomously replicated upon mitosis. Hybrid plasmids containing sequences homologous to yeast 2µ plasmid DNA can be used as well. These hybrid plasmids may be integrated by recombination into 2µ plasmids already present within the cell or may replicate autonomously. The integration vectors of EP-A-251 744 or the "disintegration" vectors of EP-A-286 424 may be used.

Any marker gene can be used in the hybrid plasmids which facilitates the selection for transformants due to the phenotypic expression of the marker. Suitable markers for yeast are particularly those expressing antibiotic resistance or, in the case of auxotrophic yeast mutants, genes which complement host lesions. Corresponding genes confer, for example, resistance to the antibiotic cycloheximide or provide for prototrophy in an auxotrophic yeast mutant, for example the URA1, URA3, ARG4, LEU2, HIS4, HIS3, TRP5 or TRP1 gene.

Advantageously, the additional DNA sequences which are present in the hybrid plasmids according to the invention also include a replication origin and a selective genetic marker for a bacterial host, especially Escherichia coli. There are useful features which are associated with the presence of an E. coli replication origin and an E. coli marker in a yeast hybrid plasmid. Firstly, large amounts of hybrid plasmid DNA can be obtained by growth and amplification in E. coli and, secondly, the construction of hybrid plasmids is conveniently done in E. coli making use of the whole repertoire of cloning technology based on E. coli. E. coli plasmids, such as pBR322 and the like, contain both E. coli replication origin and E. coli genetic markers conferring resistance to antibiotics, for example tetracydine and ampicillin, and are advantageously employed as part of the subject yeast hybrid vectors.

The hybrid vectors according to the invention may contain one or multiple DNA inserts each comprising, inter alia, the expression control sequence and the DNA sequence encoding the desired protein. If the hybrid vectors contain multiple DNA inserts, for example 2 to 4 DNA inserts, these can be present in a tandem array or at different locations of the hybrid vector. Preferred hybrid vectors contain one DNA insert or DNA inserts in a tandem array. The DNA inserts are especially head to tail arranged.

The hybrid plasmids according to the invention are prepared by methods known in the art. The process for the preparation of the hybrid vectors comprises introducing one or multiple DNA constructs containing a promoter of the invention, a DNA segment consisting of a DNA sequence coding for a desired polypeptide which DNA segment is under transcriptional control of said expression control sequence, and a DNA sequence containing fungal transcription termination signals, as such or introducing the components of said DNA constructs successively in the predetermined order into a vector DNA.

The construction of the hybrid plasmids according to the invention is performed applying conventional ligation techniques. The components of the plasmids are linked through common restriction sites and/or by means of synthetic linker molecules and/or by blunt end ligation.

A promoter of the invention may be used in transformed yeast, for example Saccharomyces cerevisiae or Schizosaccharomyces pombe, or in any other host in which the promoter is found to be effective. Fungal cells include the genera Pichia, Saccharomyces, Kluyveromyces, Candida, Torulopsis, Hansenula, Schizosaccharomyces, Citeromyces, Pachysolen, Debaromyces, Metschunikowia, Rhodosporidium, Leucosporidium, Botryoascus, Sporidiobolus, Endornycopsis, and the like. Preferred genera are those selected from the group consisting of Pichia, Saccharomyces, Kluyveromyces, Yarrowia and Hansenula, because the ability to manipulate the DNA of these yeasts has, at present, been more highly developed than for the other genera mentioned above. Examples of Saccharomyces are *Saccharomyces cerevisiae*, *Saccharomyces italicus* and *Saccharomyces rouxii*. Examples of Kluyveromyces are *Kluyveromyces fragilis* and *Kluyveromyces lactis*. Examples of Hansenula are *Hansenula polymorpha*, *Hansenula anomala* and *Hansenula capsulata*. Examples of Pichia are *Pichia pastoris* and *Pichia angusta*. *Yarrowia lipolytica* is an example of a suitable Yarrowia species. Filamentous fungi include *Aspergillus niger*.

Fungal cells can be transformed by: (a) digestion of the cell walls to produce spheroplasts; (b) mixing the spheroplasts with transforming DNA (derived from a variety of sources and containing both native and non-native DNA sequences); and (c) regenerating the transformed cells. The regenerated cells are then screened for the incorporation of the transforming DNA.

It has been demonstrated that fungal cells of the genera Pichia, Saccharomyces, Kluyveromyces, Yarrowia and Hansenula can be transformed by enzymatic digestion of the cells walls to give spheroplasts; the spheroplasts are then mixed with the transforming DNA and incubated in the presence of calcium ions and polyethylene glycol, then transformed spheroplasts are regenerated in regeneration medium.

Methods for the transformation of *S. cerevisiae* are taught generally in EP 251 744, EP 258 067 and WO 90/01063, all of which are incorporated herein by reference.

Alternatively, the transformation of yeast with the subject hybrid vectors may be accomplished according to the method described by Hinnen et al [*Proc. Natl. Acad. Sci. USA* 75, 1929 (1978)]. This method can be divided into three steps:

(1) Removal of the yeast cell wall or parts thereof using various preparations of glucosidases, such as snail gut juices (e.g. Glusulase$^R$ or Helicase$^R$) or enzyme mixtures obtained from microorganisms (eg Zymolyase$^R$) in osmotically stabilized solutions (eg 1M sorbitol).

(2) Treatment of the "naked" yeast cells (spheroplasts) with the DNA vector in the presence of PEG (polyethyleneglycol) and Ca$^{2+}$ ions.

(3) Regeneration of the cell wall and selection of the transformed cells in a solid layer of agar. This regeneration is conveniently done by embedding the spheroplasts into agar. For example, molten agar (about 50° C.) is mixed with the spheroplasts. Upon cooling the solution to yeast growth temperatures (about 30° C.), a solid layer is obtained. This agar layer is to prevent rapid diffusion and loss of essential macromolecules from the spheroplasts and thereby facilitates regeneration of the cell wall. However, cell wall regeneration may also be obtained (although at lower efficiency) by plating the spheroplasts onto the surface of preformed agar layers.

Preferably, the regeneration agar is prepared in a way to allow regeneration and selection of transformed cells at the same time. Since yeast genes coding for enzymes of amino acid biosynthetic pathways are generally used as selective markers (-supra), the regeneration is preferably performed in yeast minimal medium agar. If very high efficiencies of regeneration are required the following two step procedure is advantageous: (1) regeneration of the cell wall in a rich complex medium, and (2) selection of the transformed cells by replica plating the cell layer onto selective agar plates.

When the DNA vector is a linear DNA vector used for transforming eukaryotic host cells, transformation is preferably done in the presence of a second vector containing a selective marker for yeast. This cotransformation allows enrichment for those host cells which have taken up DNA that cannot be directly selected for. Since competent cells take up any type of DNA a high percentage of cells transformed with a selective vector will also harbor any additional DNA (such as the above linear DNA vector). The transformed host cells can be improved in production of the desired polypeptide by mutation and selection using methods known in the art. The mutation can be effected, for example, by U.V. irradiation or suitable chemical reagents. Strains which are deficient in protease A and B are particularly preferred; such strains are generally available.

The heterologous polynucleotide portion of a cloning vector or an expression vector in accordance with the present invention may encode any desired polypeptide, including oligopeptides. The polypeptide may be fibronectin or a portion thereof (for example the collagen or fibrin-binding portions described in EP 207 751 ), urokinase, pro-urokinase, the 1-368 portion of CD4 (D Smith et al (1987) *Science* 328, 1704–1707) platelet derived growth factor (Collins et al (1985) *Nature* 316, 748–750), transforming growth factor β (Derynck et al (1985) *Nature* 316, 701–705), the 1-272 portion of Von Willebrand's Factor (Bontham et al, *Nucl. Acids Res.* 145, 7125–7127), the Cathepsin D fragment of fibronectin (585–1578), α1-antitrypsin, plasminogen activator inhibitors, factor VIII, α-globin, β-globin, myoglobin, nerve growth factor, LACI (lipoprotein-associated coagulation inhibitor) (Broze, G. J. (1990) *Biochem.* 29, 7539–7546), lactoferrin (Fletcher, J. in "Iron in Immunity, Cancer & Inflammation" 1989, Wiley & Sons, Eds. de Sousa, M. & Brock, J. H.) or platelet-derived endothelial cell growth factor (PDECGF) (Ishikawa, F. (1989) *Nature* 338, 557–562), or a conservative variant of any of these. The polynucleotide may also be a fusion of human serum albumin (HSA) or an N-terminal portion thereof and any other polypeptide, such as those listed above. Preferably, the polypeptide is a naturally-occurring human serum albumin, a modified human serum albumin or a fragment of either, such modified forms and fragments being termed "variants", or is α- or β-globin. These variants include all forms or fragments of HSA which fulfill at least one of the physiological functions of HSA and which are sufficiently similar to HSA, in terms of structure (particularly tertiary structure) as to be regarded by one skilled in the art as variants or fragments of HSA. Microorganisms transformed with heterologous polynucleotides encoding the amino acid sequence of HSA produce recombinant human albumin (rHA).

Particularly preferred variants or fragments of HSA are those which retain at least 50% of its ligand-binding properties (preferably 80%, or 95%), for example with respect to bilirubin or fatty acids, and/or at least 50% (preferably 80% or 90%) of its oncotic action. Such properties are discussed in Brown, J R & Shockley, P (1982) in *Lipid-Protein Interactions* 1, 26–68, Ed. Jost, P C & Griffith, O H. An example of a useful fragment of HSA which may be expressed by use of a promoter of the invention is that disclosed in EP 322 094, the disclosure of which is incorporated herein by reference.

The polypeptide may initially be expressed as a fusion with a secretion leader sequence. In the case of HSA, this may, for example, be the natural HSA leader, the leader from the *S. cerevisiae* α mating factor, the *Kluyveromyces lactis* killer toxin leader or a fusion between the natural HSA leader and either of the said yeast leaders. Thus, the leader may be either of SEQ ID NO: 4 and SEQ ID NO: 5 or conservatively modified variations of either sequence, as described in WO 90/01063.

The host cell may be fermented to express the desired polypeptide in known ways. The polypeptide may be purified by known techniques, for example (if the polypeptide is not secreted), separating off the cells, lysing them, collecting the supernatant, concentrating it and chromatographically separating the polypeptide.

The promoter of the invention is de-repressed by the absence of carbon catabolite-repressing energy sources, such as sucrose or glucose, (whether or not glycerol and ethanol are present), which is advantageous in large scale yeast culture. Thus, the invention provides a process for growing the transformed yeast to a high mass in the presence of high levels of such a repressing carbon source, preferably sucrose, and then inducing expression of the desired polypeptide by allowing the medium to become exhausted of the repressing carbon source and adding a simpler, non-repressing carbon source, such as glycerol or ethanol.

The preferred aspects of the invention will now be described by way of representative examples and with reference to the drawings.

Strains and Culture Conditions

*Escherichia coli* DH5α (F–, φ80d/acZdeltaM15,delta (lacZYA-argF) U169, recA1, endA1, hsdR17 ($r_k$–, $m_k$+), supE44, lambda, thi-1, gyrA, relA1 ) was used for plasmid constructions. *E. coli* XL1-blue (Stratagene, endA1, hsdR17 (rk–, ink+), supE44, thi-1, lambda, recA1, gyrA96, relA1, (lac-), [F', proAB, lacI$^q$ ZΔM15, Tn10, (tet$^r$)]was used for the propagation of M13 vectors. *Saccharomyces cerevisiae* strains DB1 [cir°, a, leu2], DS65 [cir°, a, leu2], DS212 [cir°, a, leu2], DS212 pep⁻[cir°, a, leu2, pra1] and DS569 [cir°, a, leu2, pra1] were used as the recombinant albumin expression hosts. Yeast cells were grown at 30° C. on YEP (1% (w/v) yeast extract, 2% (w/v) bactopeptone) nutrient agar supplemented with the appropriate carbon source. *S. cerevisiae* transformants were grown in 10 ml YEP, 2% (w/v) sucrose in 50 ml conical shake flasks at 30° C., 200 rpm for 72 hours. HSA antibody plates were prepared by cooling YEP containing 1% (w/v) electrophoresis grade agarose to 50° C. Rabbit anti-human albumin antiserum (Cambio, Cambridge, United Kingdom) was then added to 2.5% (v/v) along with the appropriate carbon source and the nutrient medium poured into a Petri dish and allowed to cool.

DNA Manipulations

Standard DNA manipulation techniques were used (Maniatis et al, 1982: *Molecular Cloning, A Laboratory Manual;* Cold Spring Harbor; Sambrook et al 1989 (2nd edition). DNA fragments were routinely recovered from agarose gels by centrifugation (Vogelstein, B., *Anal. Biochem.* 160 (1987) 115–118). Radiolabelled DNA was prepared using [α-$^{32}$p]dATP (Amersham International PLC) and the random primer labelling procedure (Feinburg, A P and Vogelstein, B., *Anal. Biochem.* 137, (1984) 266–267). Restriction endonucleases, T4 DNA ligase, T4 DNA Polymerase and *E. coli* DNA polymerase I (Klenow fragment) were obtained from Boehringer-Mannheim.

The glycerol-3-phosphate dehydrogenase (GPD1) yeast promoter fragment was obtained from a genomic library of fragments obtained by BglII restriction of yeast DNA. The BglII restriction fragments are inserted into a unique BglII site of a plasmid containing the Herpes simplex thymidine kinase (TK) gene. Only when promoter fragments are cloned in front of the thymidine kinase gene will yeast transformed with this plasmid grow in the presence of folate antagonists such as sulphanilamide and amethopterin, as described by Goodey et al. *Molecular and General Genetics* 204, 505–511 (1986) which is incorporated herein by reference.

A plasmid having an active promoter was selected by measurement of thymidine kinase activity in the cell extract.

The promoter fragment was contained within a BglII restriction fragment of plasmid pXL5 (FIG. 1). A 1.48 kbp fragment of the glycerol-3-phosphate dehydrogenase promoter was sequenced (SEQ ID NO: 2). The promoter fragment was modified by the introduction of an SfiI restriction endonuclease site on the 3' end of the yeast promoter:

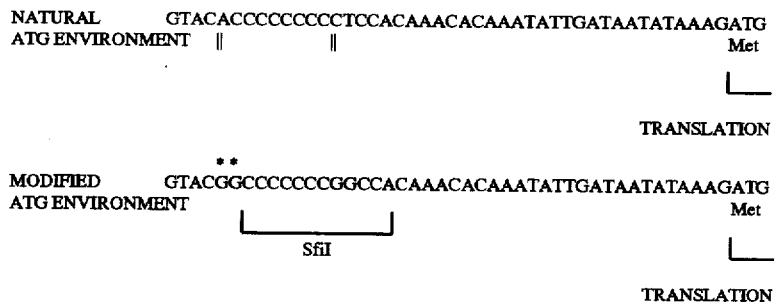

These two sequences are SEQ ID NO: 6 and SEQ ID NO: 7 respectively.

The following Examples further illustrate the invention by specific embodiment, but are not intended to be in any way limiting thereon.

EXAMPLE 1

Expression of recombinant Human Albumin (rHA)

A 282bp PstI-RsaI fragment of the promoter of the invention (ie from the CTGCAG at position 1031–1036 to the GTAC at 1314–1317 of SEQ ID NO: 1) and a 56 bp double stranded oligonucleotide linker

5'-ACGGCCCCCCCGGCCACAAACACAAATATTGATAATATAAAGATGAAGTGGGTA-5'

3' TGCCGGGGGGGCCGGTGTTTGTGTTTATAACTATTATATTTCTACTTCACCCATTCGA-3'

(the 5'-3' strand of which constitutes SEQ ID NO: 12 and the 3'-5' strand of which constitutes SEQ ID NO: 15) were inserted between the PstI and HindIII site of M13mp18 (Yanisch-Perron et al, 1985, Gene 33, 103–109) generating plasmid pAYE274 (FIG. 2), so introducing a unique SfiI site 5' to the translation initiation site. Plasmid pAYE274 was linearised with EcoRI and PstI and recircularised with the 2.3 kb EcoRI-PstI fragment from pXL5 (FIG. 1) generating pAYE275 (FIG. 3). This was digested with EcoRI-HindIII and the 2.3 kb desired promoter fragment was purified.

The construction of plasmid pAYE334, used in the next stages of the work, has been described in our co-pending UK patent application No 8927480.7 and is carried out as follows. Plasmid pAAH5 (Goodey et al. 1987: In Yeast Biotechnology, 401–429, Edited by Berry, D. R., Russell, I. and Stewart, G. G. Published by Allen and Unwin) was linearised by partially digesting with BamHI. The 5' protruding ends were blunt-ended with T4 DNA polymerase and ligated with the double-stranded oligonucleotide linker:

NotI

Figure 4:
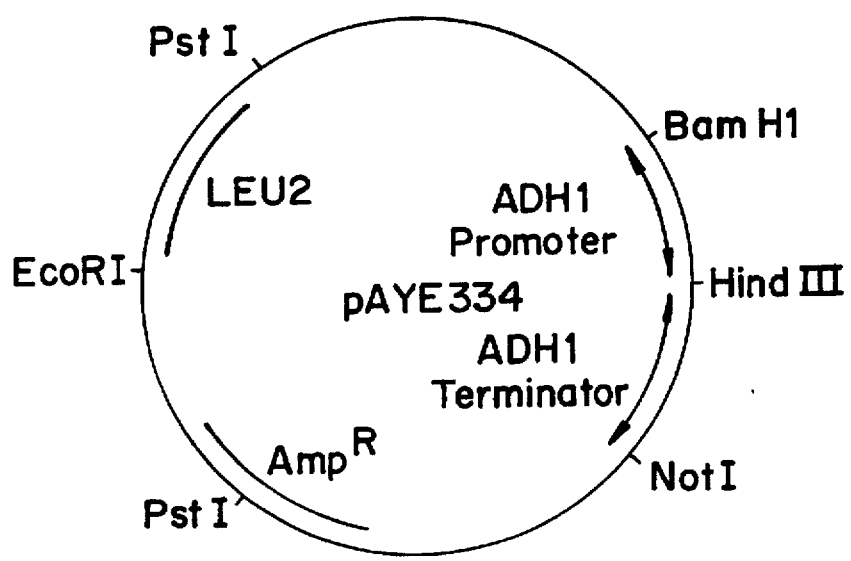

A recombinant plasmid pAYE334 (FIG. 4) was selected in which a NotI restriction site had replaced the BamHI site at the 3' end of the ADH1 terminator.

Figure 5:
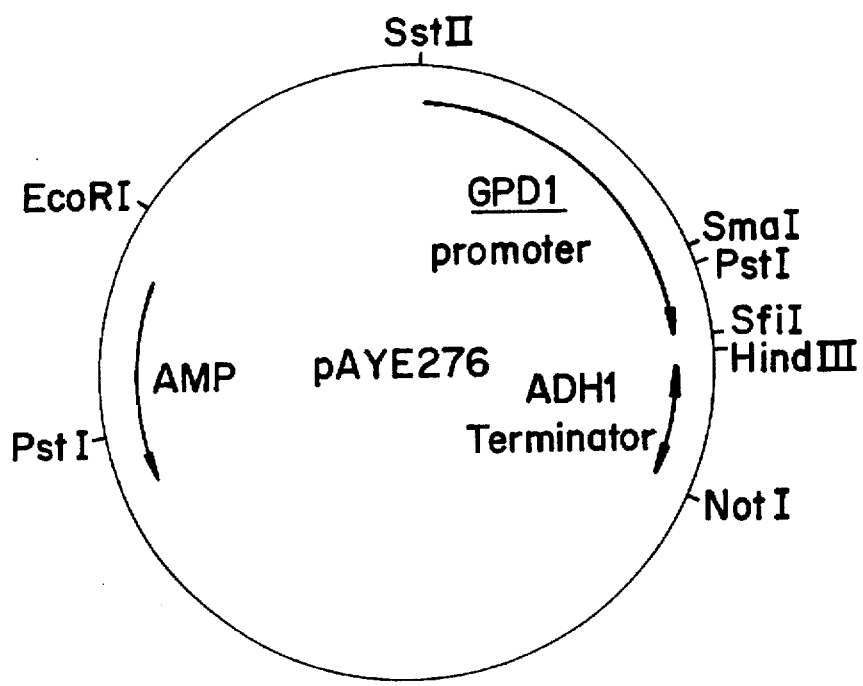

The modified promoter fragment from pAYE275 (FIG. 3) and a 450 bp HindIII-NotI ADH1 terminator fragment from pAYE334 were ligated into pAT153 (Twigg and Sherratt, 1980 Nature 283, 216–218) which itself had been modified by the introduction of a NotI recognition site (5'-GCGGCCGC-3') into and so destroying the BamHI site, generating pAYE276 (FIG. 5).

Figure 6:
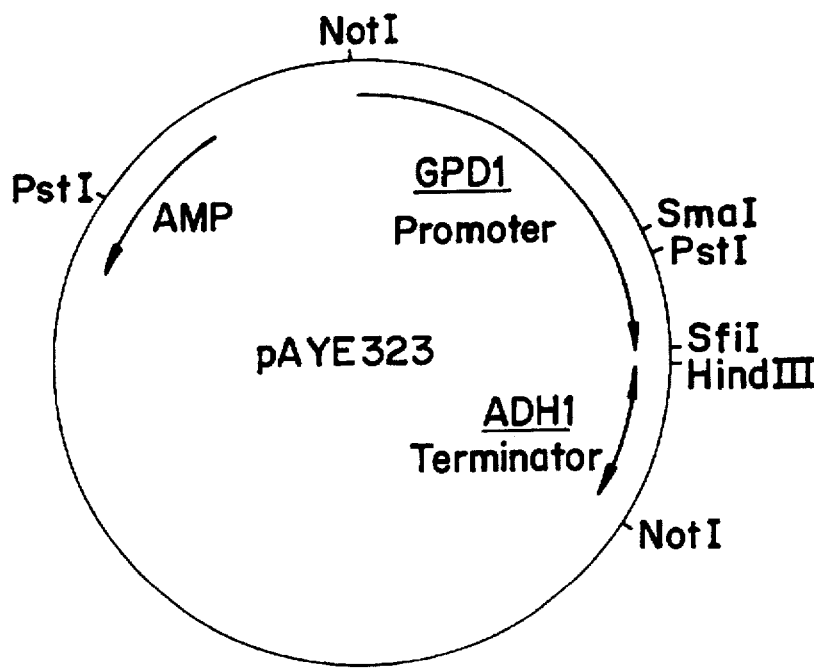

Plasmid pAYE276 was linearised with EcoRI-SstII, the 3' recessed ends filled in with T4 DNA Polymerase and dNTP and recircularised with excess NotI linker (5'-GCGGCCGC-3') generating plasmid pAYE323 (FIG. 6). This plasmid was linearised with HindIII and recircularised with a double stranded oligonucleotide linker:

in EP 286424. The LEU2 selectable marker is a 1.95 kbp SalI-HpaI fragment from YEp13, (Broach J R, et al (1979) Cell 16, 827–839) inserted into the SnaBI site of pSAC3. The LEU2 gene possesses a unique Tth111I site. Following digestion with this enzyme the 5' protruding ends were removed by treatment with the Klenow fragment of E. coli DNA Polymerase I. The insertion of a NotI recognition site to generate pSAC35 was achieved by ligating the blunt end linearised DNA with a double stranded oligonucleotide of the sequence,

Those skilled in the art will recognise a large number of techniques for modifying DNA segments which code for a wide variety of proteins for insertion into an SfiI restriction site.

This Example describes an rHA secretion vector (pAYE321) incorporating a promoter of the invention. This vector has been used to transform five different yeast strains: all five strains secreted rHA into the culture supernatant. The timing of rHA expression under the control of the promoter has also been studied. rHA mRNA is first detected when the cells have reached late logarithmic growth. High levels of rHA mRNA are maintained even when the culture has entered stationary phase.

Plasmid pAYE324 (FIG. 7) is a pAT153-based vector which possesses the entire promoter/rHA secretion cassette flanked by NotI restriction sites. The 3.715 kbp secretion cassette contains the following features:

i) A 1.35 kbp promoter fragment which includes the native promoter ATG environment except that four nucleotide substitutions have been incorporated at a site between 30 and 40bp upstream of the ATG as described above (SEQ7). These substitutions introduce a unique SfiI restriction site in the 3' region of the promoter.

ii) The natural HSA/α-factor fusion leader sequence (WO 90/01063) directing the secretion of mature rHA.

iii) The yeast alcohol dehydrogenase ADH1 terminator region.

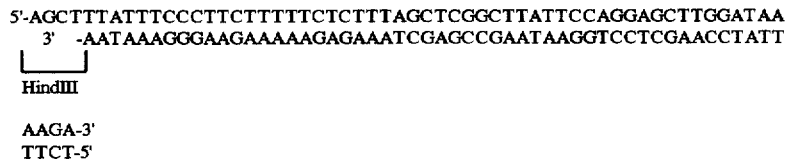

Figure 7:
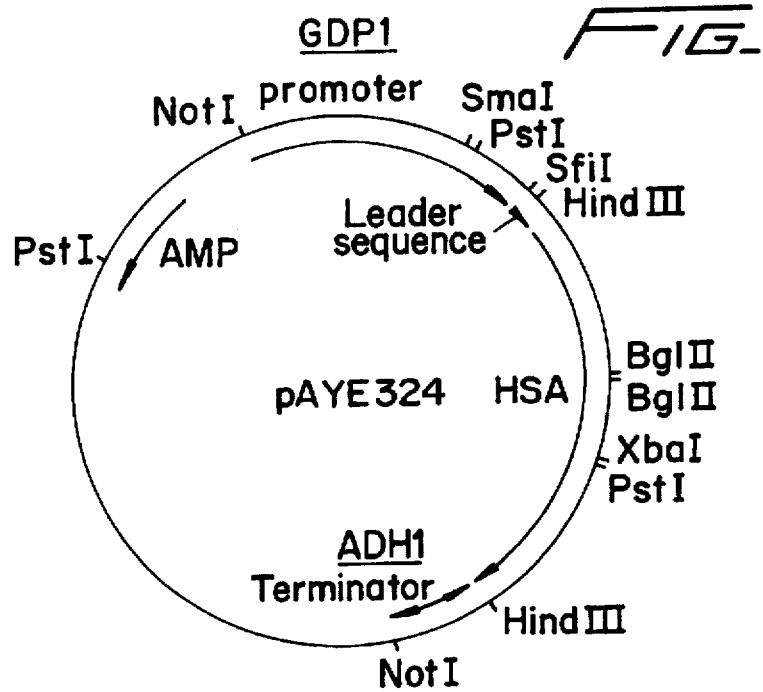
Figure 8:
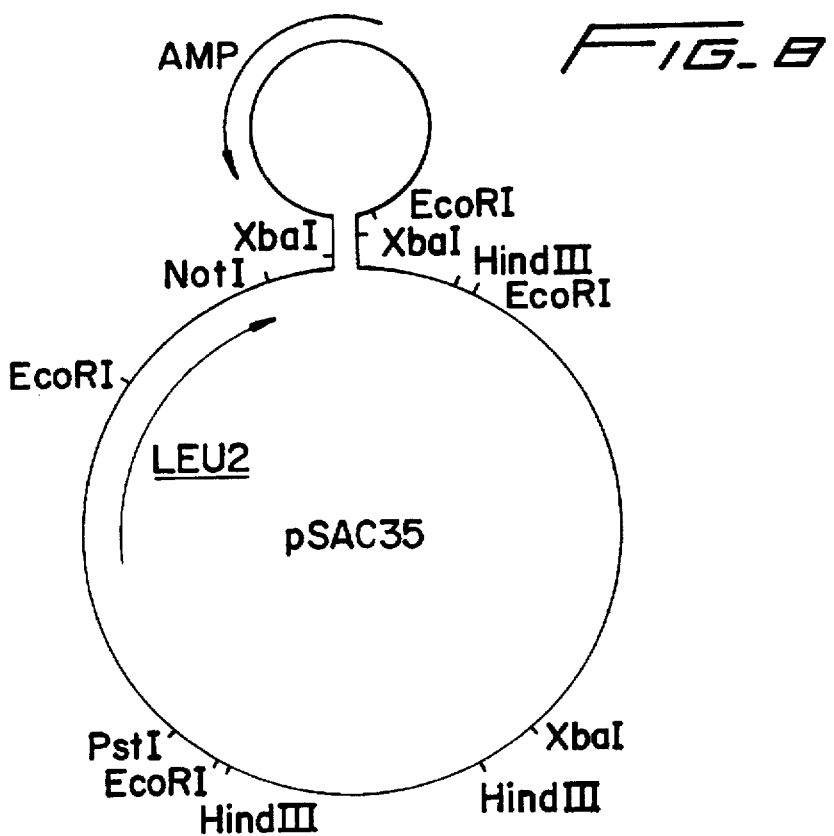
Figure 9:
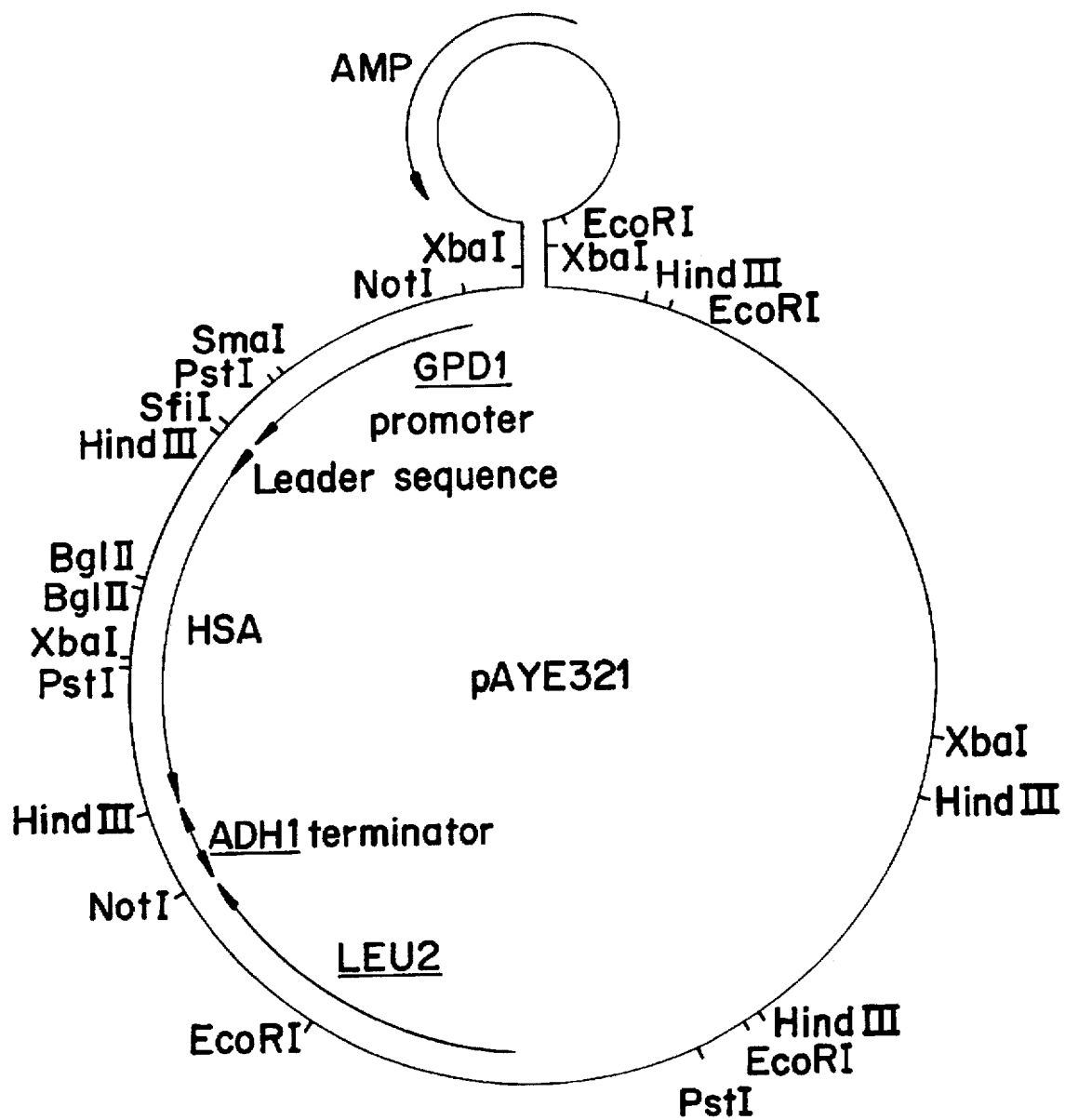

(the 5'-3' strand of which constitutes SEQ ID NO: 13 and the 3'-5' strand of which constitutes SEQ ID NO: 16) and a 1.9 kbp HA cDNA fragment liberated from XhoI linearised mp19.7 (EP-A;201 239), blunt ended with S1 nuclease and then digested with HindIII, to create plasmid pAYE324 (FIG. 7). The 3.72 kbp NotI restriction fragment created in plasmid pAYE324 (FIG. 7) may then be transferred into a suitable yeast replicating vector that contains a unique restriction site (for example pSAC35, FIG. 8), to create a plasmid such as pAYE321 (FIG. 9).

Plasmid pSAC35 is a derivative of pSAC3 described by Chinery and Hinchliffe (1989) Curr. Genet. 16, 21–25, and The 3.715 kbp NotI promoter/rHA secretion cassette was purified and inserted into the unique NotI cloning site of pSAC35 (FIG. 8) to generate plasmid pAYE321 (FIG. 9).

Five [cir°] strains were transformed to leucine prototrophy with plasmid pAYE321, namely DB1 [cir°], DS65 [cir°], DS212 [cir°], DS212 pep⁻ [cir°] and DS569 [cir°]. Transformation was performed essentially as described by Beggs (Nature, 275 (1978) 104–109) except for the following modifications. Transforming DNA in 10 μl deionised H₂O was gently mixed with 50 μl of spheroplasts in 1.2M sorbitol, 10 mM CaCl₂ and 12.5 μl 20% (w/v) PEG 3350 (Sigma), 10 mM CaCl2, 10 mM Tris/HCl (pH7.5) and held on ice for 15 minutes. After adding a further 500 μl of 20% (w/v) PEG 3350, 10 mM CaCl₂, 10 mM Tris/HCl (pH7.5) the spheroplasts were gently mixed with 5 ml of 1.2M sorbitol selective agar medium and plated out. Two independent transformants from each strain agar grown for 72 hours, 200 rpm shaking, at 30° C. in 10 ml of YEP (1% w/v yeast extract, 2% w/v bactopeptone and 2% w/v glucose).

rHA was detected in the culture supernatants of all the transformants by rocket gel immuno-electrophoresis, showing that the promoter can direct the expression/secretion of heterologous proteins in yeast.

EXAMPLE 2

Timing of Expression

A one-liter shake flask containing 400 ml of YEP, 2% (w/v) glucose was inoculated with DB1 [cir° pAYE321] and incubated at 30° C., 200 rpm. Samples (20 ml) were removed at 24 hours, 48 hours, 72 hours, 96 hours and 120 hours post inoculation. At each time point, the optical density of the culture and secreted rHA were determined. The sample was then separated by centrifugation into a cell pellet and culture supernatant. The level of rHA secreted into the supernatant was measured by rocket gel immuno-electrophoresis and RNA was extracted from the cell pellet. The RNA from each time point was separated into its individual components by gel electrophoresis, Northern blotted and probed with radio-labelled DNA homologous to the PGK and rHA structural genes. RNA was extracted from yeast cells as described by Linquist (*Nature* 293 (1981) 311–314). 10 μg of total yeast RNA was resolved on a 1.0% agarose-formaldehyde gel and vacuum blotted from 20×SSPE onto a Pall bio-dyne nylon membrane, and UV cross-linked according to Kroczek and Siebet (*Anal. Biochem.* 184 (1990) 90–95). Hybridisation was performed at 6×SSPE, 5×Denhardts, 0.1% (w/v) SDS, 100 μg/ml denatured herring sperm DNA, at 50° C. for 18 hours. Washing stringency was 0.2>SSPE, 0.1% (w/v) SDS, 50° C.

The results are illustrated in FIG. 10. FIG. 11 shows the optical density and level of rHA during the experiment. At the first timepoint 24 hrs post inoculation, PGK mRNA is observed; however, neither secreted rHA nor HA mRNA are detected. At the second time point, 48 hrs post inoculation, both PGK and HA mRNA are detected within the cell. The HA mRNA is available for translation because secreted rHA is observed in the culture supernatant. At the next three time points, 72 hrs, 96 hrs and 120 hrs post inoculation, only HA mRNA is observed and the PGK mRNA has disappeared. The level of rHA observed in the culture supernatant has increased from the previous time point, but no further increase is observed. The following conclusions can be drawn:

i) The HA cDNA (under the control of the GPD1 promoter) is not expressed during the early growth phase and does not mirror PGK expression.

ii) The HA cDNA (under the control of the GPD1 promoter) is expressed and rHA is secreted during the late logarithmic and stationary growth phase.

iii) mRNA levels are maintained during stationary phase.

Furthermore, the timing of expression can be manipulated in the controlled environment of a fermentation vessel, be it batch, fed-batch or continuous culture. When carbon catabolite-repressing sources such as sucrose or glucose are supplied as the sole carbon source, the expression of the heterologous protein is repressed. Consequently the growth of the host organism is not impaired by the synthesis of the heterologous protein. At a point predetermined by the operator, or when the sucrose or glucose is exhausted, it is replaced by a non-repressing carbon source such as glycerol or ethanol. Under these conditions, the expression of the heterologous protein is de-repressed. Consequently, production can be regulated in such a way as to optimize the synthesis of the desired product.

EXAMPLE 3

Expression with various carbon sources

DB1 [cir° pAYE321] was grown for 72 hrs in 10 ml YEP, 200 rpm, 30° C. supplemented with various carbon sources. In the control experiment sucrose is supplied instead of glucose but the final rHA secretion levels are identical. In all the other experiments a stimulation of rHA secretion is observed. The results are given in Table 1 below. The best carbon source would appear to be a combination of 1% (v/v) ethanol and 1% (v/v) glycerol. Although the-stimulating effect at first sight does not appear very great it must be remembered that the value achieved on sucrose as a carbon source is really the value achieved on a mixture of sucrose and ethanol since fermentative growth generates ethanol and acetate which are utilized by the yeast upon exhaustion of the sucrose. If the culture was maintained in sucrose excess (7% w/v sucrose at the beginning), the level of secreted rHA was reduced several fold.

TABLE 1

| Carbon Source | | | rHA secreted into |
|---|---|---|---|
| % sucrose (w/v) | % glycerol (v/v) | % ethanol (v/v) | culture supernatant (arbitrary units) |
| 2.0 | — | — | 7.5 |
| — | 2.0 | — | 9.0 |
| — | — | 2.0 | 9.5 |
| — | 1.5 | 0.5 | 10.5 |
| — | 1.0 | 1.0 | 12.5 |
| — | 0.5 | 1.5 | 11.0 |

EXAMPLE 4

This example describes plasmid pDVX4 designed for expressing and secreting the *S. cerevisiae var diastaticus* glucoamylase.

Construction of Plasmid pDVX4

The initial step involved the construction of a generalised brewing yeast vector pDXL200 (FIG. 12) which contained the following DNA sequences:

a) 0.34 kbp SmaI-SfiI fragment of the modified GPD1 promoter (pAYE275).

b) A synthetic oligonucleotide linker containing restriction enzyme sites for SfiI, BglII and HindIII:

Synthetic Oligonucleotide Linker

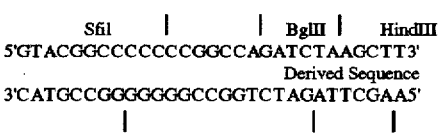

-continued

Oligos 5'  CGGCCAGATCTA3' (12)
Synthesized: 3'GGGGCCGGTCTAGATTCGA5' (19)

The 5'-3' modified region and the two oligonucleotides are listed as SEQ ID NO. 14, SEQ ID NO: 8 and SEQ ID NO: 9 respectively and the 3'-5' region of which is listed as SEQ ID NO: 17.

c) 0.45 kbp of the ADH1 terminator (Hitzeman, R A et al, (1981). *Nature*. 293, 717.)

d) The CUP1 gene and its flanking sequences from *S. cerevisiae* were present on 0.7 kbp KpnI-XbaI fragment and 0.38 kbp BamHI-KpnI fragment respectively (Karin, M et al, (1984). *Proc. Natl. Acad. Sci. USA* 81, 337.). The CUP-1 gene was used as a selective genetic marker for brewing yeast transformation.

e) 2.7 kbp of bacterial DNA (pUC9) as present in pSAC3 (Chinery and Hinchliffe (1989) *Curr. Genet.* 16, 21–25).

f) 2 μm DNA: 2.2 kbp HindIII fragment containing the 2 μm origin of replication (Broach, J R (1982). The yeast plasmid 2 μm circle. In "The Molecular Biology of the yeast *Saccharomyces cerevisiae:* Life Cycle and Inheritance". Eds. Strathern, J N, E W Jones and J R Broach). Cold Spring Harbor, p445.) The full DNA sequence of 2 μm DNA is also known (Hartley, J L and Donelson, J E (1980). *Nature*. 226, 860).

The DEX1 gene which codes for glucoamylase was isolated from *S. cerevisiae vat diastaticus* (Meaden P K et al, (1985) *Gene*. 34, 325 and PCT/GB85/00599; Pardo et al (1988 *FEBS. Lett.* 239, 179–184 describe the DEX1 promoter and part of the open reading frame). A 2.75 kbp BglII fragment carrying the DEX1 gene was cloned into the unique BglII site in pDXL200 and the DNA sequence is represented as SEQ ID NO: 10, with the protein encoded thereby appearing as SEQ ID NO: 11. The resulting plasmid, pDVX2 (FIG. 13), was digested with XbaI to remove the smaller fragment (2.7 kbp) containing the bacterial DNA.

After gel purification, the larger XbaI fragment was transformed into brewing yeast and this plasmid designated pDVX4 (FIG. 14).

Expression of DEX1

Brewing yeast strains transformed to copper resistance with plasmid pDVX4 were assayed for glucoamylase production by measuring glucose released from starch using the hexokinase-UV assay (Boehringer-Mannheim). In all cases copper resistant transformants produced significant quantities of extracellular glucoamylase.

EXAMPLE 5

Comparison of Promoters

The activity of the GPD1 promoter of the invention was compared to that of the PGK1 promoter which is described in the literature as having high efficiency, i.e. strength and transcription capacity, Kingsman et al. 1990 *Methods Enzymol*. 185, pp329–341. Yeast DB1 [cir°] and DS569 [cir°] from Example 1 were transformed as described therein with analogous plasmids differing only in the promoters to be compared. The transformed yeasts were utilized to express rHA as in Example 1 using sucrose as the carbon source. The results, shown below, clearly indicate that the subject promoter possesses superior efficiency to the PGK1 promoter.

| Transformed Strain | Promoter | Secreted rHA (mg/L) |
| --- | --- | --- |
| DB1 [cir°] | GPD1 | 20–30 |
|  | PGK1 | 1–5 |
| DS569 [cir°] | GPD1 | 60–70 |
|  | PGK1 | 35–45 |

We claim:

1. An isolated or synthetic promoter selected from the group consisting of the nucleic acid set forth as SEQ ID NO: 1 and a variant thereof, which variant:
   (i) is at least 100 nucleotides long;
   (ii) has at least 80% sequence identity with a fragment of SEQ ID NO: 1 which has the same length as the variant;
   (iii) retains at least 10% of the transcription rate capacity of the nucleic acid set forth as SEQ ID NO: 1; and
   (iv) is repressed by sucrose or glucose and derepressed by the absence of sucrose or glucose.

2. The isolated or synthetic promoter according to claim 1, wherein said variant has at least 80% of the transcription rate capacity of the nucleic acid of SEQ ID NO: 1.

3. A vector comprising the isolated or synthetic promoter according to claim 1.

4. A vector comprising the isolated or synthetic promoter according to claim 2.

5. The vector according to claim 3, wherein the isolated or synthetic promoter is operably linked to a nucleotide sequence encoding a polypeptide.

6. The vector according to claim 4, wherein the isolated or synthetic promoter is operably linked to a nucleotide sequence encoding a polypeptide.

7. The vector according to claim 5, wherein the polypeptide is human serum albumin or a variant thereof.

8. The vector according to claim 5, wherein the polypeptide is glucoamylase of *Saccharomyces cerevisiae var. diastaticus*.

9. A yeast cell transformed with the vector according to claim 5.

10. A yeast cell transformed with the vector according to claim 7.

11. A process for preparing a polypeptide, comprising culturing the yeast cell of claim 9, thereby expressing the polypeptide encoded by the nucleotide sequence, and at least partially purifying the polypeptide.

12. The process according to claim 11, wherein the yeast cell is initially cultured on a carbon source or sources which repress expression of the polypeptide and the yeast cell is subsequently cultured on a non-repressing carbon source or sources.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 1357 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Saccharomyces cerevisiae ( i x ) FEATURE:
        ( A ) NAME/KEY: promoter
        ( B ) LOCATION: 42..52
        ( D ) OTHER INFORMATION: /function="RNA POLIII promoter box A"

( i x ) FEATURE:
    ( A ) NAME/KEY: promoter
    ( B ) LOCATION: 86..96
    ( D ) OTHER INFORMATION: /function="RNA POLIII
        Promoter box B"

( i x ) FEATURE:
    ( A ) NAME/KEY: promoter
    ( B ) LOCATION: 113..118
    ( D ) OTHER INFORMATION: /function="RNA POLIII
        Terminator"

( i x ) FEATURE:
    ( A ) NAME/KEY: protein_bind
    ( B ) LOCATION: 1091..1103
    ( D ) OTHER INFORMATION: /bound_moiety=
        " RAP1/GRF1/TUF1"

( i x ) FEATURE:
    ( A ) NAME/KEY: protein_bind
    ( B ) LOCATION: 1106..1118
    ( D ) OTHER INFORMATION: /bound_moiety=
        " RAP1/GRF1/TUF1"

( i x ) FEATURE:
    ( A ) NAME/KEY: misc_signal
    ( B ) LOCATION: 1176..1241
    ( D ) OTHER INFORMATION: /function="Pyrimidine (CT)
        block"

( i x ) FEATURE:
    ( A ) NAME/KEY: TATA_signal
    ( B ) LOCATION: 1326..1335

( i x ) FEATURE:
    ( A ) NAME/KEY: misc_signal
    ( B ) LOCATION: 1246..1283
    ( D ) OTHER INFORMATION: /function="Pyrimidine (CT)
        block"

( i x ) FEATURE:
    ( A ) NAME/KEY: misc_signal
    ( B ) LOCATION: 1295..1298
    ( D ) OTHER INFORMATION: /function="CAAG box"

( i x ) FEATURE:
    ( A ) NAME/KEY: misc_signal
    ( B ) LOCATION: 1302..1306
    ( D ) OTHER INFORMATION: /function="CAATT box"

( i x ) FEATURE:
    ( A ) NAME/KEY: misc_feature
    ( B ) LOCATION: 1031..1036
    ( D ) OTHER INFORMATION: /function="PstI restriction site"

( x i ) SEQUENCE DESCRIPTION: SEQ ID NO:1:

```
CCGCGGTGCC GAGATGCAGA CGTGGCCAAC TGTGTCTGCC GTCGCAAAAT GATTTGAATT      60
TTGCGTCGCG CACGTTTCTC ACGTACATAA TAAGTATTTT CATACAGTTC TAGCAAGACG     120
AGGTGGTCAA AATAGAAGCG TCCTATGTTT TACAGTACAA GACAGTCCAT ACTGAAATGA     180
CAACGTACTT GACTTTTCAG TATTTTCTTT TTCTCACAGT CTGGTTATTT TTGAAAGCGC     240
ACGAAATATA TGTAGGCAAG CATTTTCTGA GTCTGCTGAC CTCTAAAATT AATGCTATTG     300
TGCACCTTAG TAACCCAAGG CAGGACAGTT ACCTTGCGTG GTGTTACTAT GGCCGGAAGC     360
CCGAAAGAGT TATCGTTACT CCGATTATTT TGTACAGCTG ATGGGACCTT GCCGTCTTCA     420
TTTTTTTTTT TTTTCACCTA TAGAGCCGGG CAGAGCTGCC CGGCTTAACT AAGGGCCGGA     480
AAAAAAACGG AAAAAGAAA  GCCAAGCGTG TAGACGTAGT ATAACAGTAT ATCTGACACG     540
CACGTGATGA CCACGTAATC GCATCGCCCC TCACCTCTCA CCTCTCACCG CTGACTCAGC     600
TTCACTAAAA AGGAAAATAT ATACTCTTTC CAGGCAAGG  TGACAGCGGT CCCCGTCTCC     660
TCCACAAAGG CCTCTCCTGG GGTTTGAGCA AGTCTAAGTT TACGTAGCAT AAAAATTCTC     720
```

-continued

| | | | | | |
|---|---|---|---|---|---|
| GGATTGCGTC | AAATAATAAA | AAAAGTAACC | CCACTTCTAC | TTCTACATCG | GAAAAACATT | 780
| CCATTCACAT | ATCGTCTTTG | GCCTATCTTG | TTTTGTCCTC | GGTAGATCAG | GTCAGTACAA | 840
| ACGCAACACG | AAAGAACAAA | AAAGAAGAA | AACAGAAGGC | CAAGACAGGG | TCAATGAGAC | 900
| TGTTGTCCTC | CTACTGTCCC | TATGTCTCTG | GCCGATCACG | CGCCATTGTC | CCTCAGAAAC | 960
| AAATCAAACA | CCCACACCCC | GGGCACCCAA | AGTCCCCACC | CACACCACCA | ATACGTAAAC | 1020
| GGGGCGCCCC | CTGCAGGCCC | TCCTGCGCGC | GGCCTCCCGC | CTTGCTTCTC | TCCCCTTCCT | 1080
| TTTCTTTTTC | CAGTTTTCCC | TATTTGTCC | CTTTTCCGC | ACAACAAGTA | TCAGAATGGG | 1140
| TTCATCAAAT | CTATCCAACC | TAATTCGCAC | GTAGACTGGC | TTGGTATTGG | CAGTTTCGTA | 1200
| GTTATATATA | TACTACCATG | AGTGAAACTG | TTACGTTACC | TTAAATTCTT | TCTCCCTTTA | 1260
| ATTTTCTTTT | ATCTTACTCT | CCTACATAAG | ACATCAAGAA | ACAATTGTAT | ATTGTACACC | 1320
| CCCCCCCTCC | ACAAACACAA | ATATTGATAA | TATAAAG | | | 1357

( 2 ) INFORMATION FOR SEQ ID NO:2:

( i ) SEQUENCE CHARACTERISTICS:
        ( A ) LENGTH: 1483 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 123..124
        ( D ) OTHER INFORMATION: /product="SstII restriction site"

( x i ) SEQUENCE DESCRIPTION: SEQ ID NO:2:

| | | | | | |
|---|---|---|---|---|---|
| AAGAAAGATT | CTCGGTAACG | ACCATACAAA | TATTGGGCGT | GTGGCGTAGT | CGGTAGCGCG | 60
| CTCCCTTAGC | ATGGGAGAGG | TCTCCGGTTC | GATTCCGGAC | TCGTCCAAAT | TATTTTTTAC | 120
| TTTCCGCGGT | GCCGAGATGC | AGACGTGGCC | AACTGTGTCT | GCCGTCGCAA | AATGATTTGA | 180
| ATTTGCGTC | GCGCACGTTT | CTCACGTACA | TAATAAGTAT | TTCATACAG | TTCTAGCAAG | 240
| ACGAGGTGGT | CAAAATAGAA | GCGTCCTATG | TTTTACAGTA | CAAGACAGTC | CATACTGAAA | 300
| TGACAACGTA | CTTGACTTTT | CAGTATTTTC | TTTTTCTCAC | AGTCTGGTTA | TTTTTGAAAG | 360
| CGCACGAAAT | ATATGTAGGC | AAGCATTTTC | TGAGTCTGCT | GACCTCTAAA | ATTAATGCTA | 420
| TTGTGCACCT | TAGTAACCCA | AGGCAGGACA | GTTACCTTGC | GTGGTGTTAC | TATGGCCGGA | 480
| AGCCCGAAAG | AGTTATCGTT | ACTCCGATTA | TTTTGTACAG | CTGATGGGAC | CTTGCCGTCT | 540
| TCATTTTTTT | TTTTTTTCAC | CTATAGAGCC | GGGCAGAGCT | GCCCGGCTTA | ACTAAGGGCC | 600
| GGAAAAAAAA | CGGAAAAAAG | AAAGCCAAGC | GTGTAGACGT | AGTATAACAG | TATATCTGAC | 660
| ACGCACGTGA | TGACCACGTA | ATCGCATCGC | CCCTCACCTC | TCACCTCTCA | CCGCTGACTC | 720
| AGCTTCACTA | AAAAGGAAAA | TATATACTCT | TTCCCAGGCA | AGGTGACAGC | GGTCCCCGTC | 780
| TCCTCCACAA | AGGCCTCTCC | TGGGGTTTGA | GCAAGTCTAA | GTTACGTAG | CATAAAAATT | 840
| CTCGGATTGC | GTCAAATAAT | AAAAAAAGTA | ACCCCACTTC | TACTTCTACA | TCGGAAAAAC | 900
| ATTCCATTCA | CATATCGTCT | TTGGCCTATC | TTGTTTTGTC | CTCGGTAGAT | CAGGTCAGTA | 960
| CAAACGCAAC | ACGAAAGAAC | AAAAAAAGAA | GAAAACAGAA | GGCCAAGACA | GGGTCAATGA | 1020
| GACTGTTGTC | CTCCTACTGT | CCCTATGTCT | CTGGCCGATC | ACGCGCCATT | GTCCCTCAGA | 1080
| AACAAATCAA | ACACCCACAC | CCCGGGCACC | CAAAGTCCCC | ACCCACACCA | CCAATACGTA | 1140
| AACGGGGCGC | CCCCTGCAGG | CCCTCCTGCG | CGCGGCCTCC | CGCCTTGCTT | CTCTCCCCTT | 1200

```
CCTTTTCTTT TTCCAGTTTT CCCTATTTTG TCCCTTTTTC CGCACAACAA GTATCAGAAT    1260

GGGTTCATCA AATCTATCCA ACCTAATTCG CACGTAGACT GGCTTGGTAT TGGCAGTTTC    1320

GTAGTTATAT ATATACTACC ATGAGTGAAA CTGTTACGTT ACCTTAAATT CTTTCTCCCT    1380

TTAATTTTCT TTTATCTTAC TCTCCTACAT AAGACATCAA GAAACAATTG TATATTGTAC    1440

ACCCCCCCC TCCACAAACA CAAATATTGA TAATATAAAG ATG                       1483
```

( 2 ) INFORMATION FOR SEQ ID NO:3:

( i ) SEQUENCE CHARACTERISTICS:
        ( A ) LENGTH: 380 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: misc_feature
        ( B ) LOCATION: 54..59
        ( D ) OTHER INFORMATION: /function="PstI restriction site"

( i x ) FEATURE:
        ( A ) NAME/KEY: misc_feature
        ( B ) LOCATION: 337..340
        ( D ) OTHER INFORMATION: /function="RsaI restriction site"

( x i ) SEQUENCE DESCRIPTION: SEQ ID NO:3:

```
CCCGGGCACC CAAAGTCCCC ACCCACACCA CCAATACGTA AACGGGGCGC CCCCTGCAGG     60

CCCTCCTGCG CGCGGCCTCC CGCCTTGCTT CTCTCCCCTT CCTTTTCTTT TTCCAGTTTT    120

CCCTATTTTG TCCCTTTTTC CGCACAACAA GTATCAGAAT GGGTTCATCA AATCTATCCA    180

ACCTAATTCG CACGTAGACT GGCTTGGTAT TGGCAGTTTC GTAGTTATAT ATATACTACC    240

ATGAGTGAAA CTGTTACGTT ACCTTAAATT CTTTCTCCCT TTAATTTTCT TTTATCTTAC    300

TCTCCTACAT AAGACATCAA GAAACAATTG TATATTGTAC ACCCCCCCC TCCACAAACA    360

CAAATATTGA TAATATAAAG                                               380
```

( 2 ) INFORMATION FOR SEQ ID NO:4:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( i x ) FEATURE:
        ( A ) NAME/KEY: Peptide
        ( B ) LOCATION: 1..24
        ( D ) OTHER INFORMATION: /label=leader
                 / note= "Synthetic secretion leader sequence"

( x i ) SEQUENCE DESCRIPTION: SEQ ID NO:4:

```
Met Lys Trp Val Ser Phe Ile Ser Leu Leu Phe Leu Phe Ser Ser Ala
 1               5                  10                  15
```

Tyr  Ser  Arg  Ser  Leu  Asp  Lys  Arg
                            20

( 2 ) INFORMATION FOR SEQ ID NO:5:

( i ) SEQUENCE CHARACTERISTICS:
            ( A ) LENGTH: 21 amino acids
            ( B ) TYPE: amino acid
            ( C ) STRANDEDNESS: single
            ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( i x ) FEATURE:
            ( A ) NAME/KEY: Peptide
            ( B ) LOCATION: 1..21
            ( D ) OTHER INFORMATION: /label=leader
                    / note= "Synthetic secretion leader sequence"

( x i ) SEQUENCE DESCRIPTION: SEQ ID NO:5:

Met  Asn  Ile  Phe  Tyr  Ile  Phe  Leu  Phe  Leu  Leu  Ser  Phe  Val  Gln  Gly
        1                   5                        10                       15

Ser  Leu  Asp  Lys  Arg
                           20

( 2 ) INFORMATION FOR SEQ ID NO:6:

( i ) SEQUENCE CHARACTERISTICS:
            ( A ) LENGTH: 47 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
            ( A ) ORGANISM: Saccharomyces cerevisiae ( i x ) FEATURE:
            ( A ) NAME/KEY: exon
            ( B ) LOCATION: 1..47
            ( D ) OTHER INFORMATION: /note= "Natural ATG
                    environment of the GDP2 promoter"

( x i ) SEQUENCE DESCRIPTION: SEQ ID NO:6:

GTACACCCCC CCCCTCCACA AACACAAATA TTGATAATAT AAAGATG                                            47

( 2 ) INFORMATION FOR SEQ ID NO:7:

( i ) SEQUENCE CHARACTERISTICS:
            ( A ) LENGTH: 47 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
            ( A ) NAME/KEY: modified_base
            ( B ) LOCATION: 5

```
        ( i x ) FEATURE:
                ( A ) NAME/KEY: modified_base
                ( B ) LOCATION: 6

( i x ) FEATURE:
                ( A ) NAME/KEY: modified_base
                ( B ) LOCATION: 14

( i x ) FEATURE:
                ( A ) NAME/KEY: modified_base
                ( B ) LOCATION: 15

( i x ) FEATURE:
                ( A ) NAME/KEY: -
                ( B ) LOCATION: 5..17
                ( D ) OTHER INFORMATION: /label=SfiI
                        / note= "SfiI restriction site"

( x i ) SEQUENCE DESCRIPTION: SEQ ID NO:7:

GTACGGCCCC CCCGGCCACA AACACAAATA TTGATAATAT AAAGATG                    4 7

( 2 ) INFORMATION FOR SEQ ID NO:8:

( i ) SEQUENCE CHARACTERISTICS:
                ( A ) LENGTH: 12 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: YES ( i v ) ANTI-SENSE: NO ( i x ) FEATURE:
                ( A ) NAME/KEY: misc_feature
                ( B ) LOCATION: 1..12
                ( D ) OTHER INFORMATION: /function="synthetic oligo
                        to create SEQ14"

( x i ) SEQUENCE DESCRIPTION: SEQ ID NO:8:

CGGCCAGATC TA                                                          1 2

( 2 ) INFORMATION FOR SEQ ID NO:9:

( i ) SEQUENCE CHARACTERISTICS:
                ( A ) LENGTH: 19 base pairs
                ( B ) TYPE: nucleic acid
                ( C ) STRANDEDNESS: single
                ( D ) TOPOLOGY: linear ( i i ) MOLECULE TYPE: cDNA ( i x ) FEATURE:
                ( A ) NAME/KEY: misc_feature
                ( B ) LOCATION: 1..19
                ( D ) OTHER INFORMATION: /function="synthetic oligo
                        used to create SEQ14"
                        / note= "This oligo is complementary to SEQ8"

( x i ) SEQUENCE DESCRIPTION: SEQ ID NO:9:

AGCTTAGATC TGGCCGGGG                                                   1 9

( 2 ) INFORMATION FOR SEQ ID NO:10:

( i ) SEQUENCE CHARACTERISTICS:
                ( A ) LENGTH: 2754 base pairs
                ( B ) TYPE: nucleic acid
                ( C ) STRANDEDNESS: double
                ( D ) TOPOLOGY: linear ( i i ) MOLECULE TYPE: DNA (genomic)
```

( i i i ) HYPOTHETICAL: NO ( i v ) ANTI-SENSE: NO ( v i ) ORIGINAL SOURCE:
   ( A ) ORGANISM: Saccharomyces cerevisiae
   ( B ) STRAIN: S. cerevisiae var. diastaticus 5106-9A ( i x ) FEATURE:
   ( A ) NAME/KEY: misc_feature
   ( B ) LOCATION: 98..103
   ( D ) OTHER INFORMATION: /function="StuII/BglII site"

( i x ) FEATURE:
   ( A ) NAME/KEY: CDS
   ( B ) LOCATION: 126..2543

( x i ) SEQUENCE DESCRIPTION: SEQ ID NO:10:

```
GATCTTTTGC TTCCTAAACT AAACCTATAA AAAGCACCCT ATTCATCAGT TATAATCTCT    60

TGTCATGTTG TGGTTCTAAT TGAAAATATA CTATGGTAGG CCTCAAAAAT CCATATACGC   120

ACACT ATG CAA AGA CCA TTT CTA CTC GCT TAT TTG GTC CTT TCG CTT       167
      Met Gln Arg Pro Phe Leu Leu Ala Tyr Leu Val Leu Ser Leu
       1               5                  10

CTA TTT AAC TCA GCT TTG GGT TTT CCA ACT GCA CTA GTT CCT AGA GGA     215
Leu Phe Asn Ser Ala Leu Gly Phe Pro Thr Ala Leu Val Pro Arg Gly
 15              20                  25                  30

TCC TCC TCT AGC AAC ATC ACT TCG TCC GGT CCA TCT TCA ACT CCA TTC     263
Ser Ser Ser Ser Asn Ile Thr Ser Ser Gly Pro Ser Ser Thr Pro Phe
                 35                  40                  45

AGC TCT GCT ACT GAA AGC TTT TCT ACT GGC ACT ACT GTC ACT CCA TCA     311
Ser Ser Ala Thr Glu Ser Phe Ser Thr Gly Thr Thr Val Thr Pro Ser
             50                  55                  60

TCA TCC AAA TAC CCT GGC AGT AAA ACA GAA ACT TCT GTT TCT TCT ACA     359
Ser Ser Lys Tyr Pro Gly Ser Lys Thr Glu Thr Ser Val Ser Ser Thr
         65                  70                  75

ACC GAA ACT ACC ATT GTT CCA ACT ACA ACT ACG ACT TCT GTC ATA ACA     407
Thr Glu Thr Thr Ile Val Pro Thr Thr Thr Thr Ser Val Ile Thr
     80                  85                  90

CCA TCA ACA ACC ACT ATT ACC ACT ACG GTT TGC TCT ACA GGA ACA AAC     455
Pro Ser Thr Thr Thr Ile Thr Thr Thr Val Cys Ser Thr Gly Thr Asn
 95                 100                 105                 110

TCT GCC GGT GAA ACT ACT TCT GGA TGC TCT CCA AAG ACC ATT ACA ACT     503
Ser Ala Gly Glu Thr Thr Ser Gly Cys Ser Pro Lys Thr Ile Thr Thr
                115                 120                 125

ACT GTT CCA TGT TCA ACC AGT CCA AGC GAA ACC GCA TCG GAA TCA ACA     551
Thr Val Pro Cys Ser Thr Ser Pro Ser Glu Thr Ala Ser Glu Ser Thr
            130                 135                 140

ACC ACT TCA CCT ACC ACA CCT GTA ACT ACA GTT GTC GCA ACC ACC GTC     599
Thr Thr Ser Pro Thr Thr Pro Val Thr Thr Val Val Ala Thr Thr Val
        145                 150                 155

GTT ACT ACT GAG TAT TCT ACT AGT ACA AAA CAA GGT GGT GAA ATT ACA     647
Val Thr Thr Glu Tyr Ser Thr Ser Thr Lys Gln Gly Gly Glu Ile Thr
    160                 165                 170

ACT ACA TTT GTC ACC AAA AAC AGT CCA ACC ACT TAC CTA ACT ACA ATT     695
Thr Thr Phe Val Thr Lys Asn Ser Pro Thr Thr Tyr Leu Thr Thr Ile
175                 180                 185                 190

GCT CCA ACT TCA TCA GTC ACT ACG GTT ACC AAT TTC ACC CCA ACC ACT     743
Ala Pro Thr Ser Ser Val Thr Thr Val Thr Asn Phe Thr Pro Thr Thr
                195                 200                 205

ATT ACT ACT ACG GTT TGC TCT ACA GGA ACA AAC TCT GCC GGT GAA ACT     791
Ile Thr Thr Thr Val Cys Ser Thr Gly Thr Asn Ser Ala Gly Glu Thr
                210                 215                 220
```

-continued

| | | | | | | | | | | | | | | | | |
|---|---|---|---|---|---|---|---|---|---|---|---|---|---|---|---|---|
| ACC | TCT | GGA | TGC | TCT | CCA | AAG | ACT | GTC | ACA | ACA | ACT | GTT | CTT | TGT | TCA | 839 |
| Thr | Ser | Gly | Cys | Ser | Pro | Lys | Thr | Val | Thr | Thr | Thr | Val | Leu | Cys | Ser | |
| | | 225 | | | | 230 | | | | | 235 | | | | | |
| ACT | GGT | ACT | GGC | GAA | TAC | ACT | ACT | GAA | GCT | ACC | GCC | CCT | GTT | ACA | ACA | 887 |
| Thr | Gly | Thr | Gly | Glu | Tyr | Thr | Thr | Glu | Ala | Thr | Ala | Pro | Val | Thr | Thr | |
| | | 240 | | | | 245 | | | | | 250 | | | | | |
| GCT | GTC | ACA | ACC | ACC | GTT | GTT | ACC | ACT | GAA | TCC | TCT | ACG | GGT | ACT | AAC | 935 |
| Ala | Val | Thr | Thr | Thr | Val | Val | Thr | Thr | Glu | Ser | Ser | Thr | Gly | Thr | Asn | |
| 255 | | | | | 260 | | | | | 265 | | | | | 270 | |
| TCC | GTC | GGT | AAG | ACG | ACA | ACT | AGT | TAC | ACA | ACA | AAG | TCT | GTA | CCA | ACC | 983 |
| Ser | Val | Gly | Lys | Thr | Thr | Thr | Ser | Tyr | Thr | Thr | Lys | Ser | Val | Pro | Thr | |
| | | | | 275 | | | | 280 | | | | | 285 | | | |
| ACC | TAT | GTA | TTT | GAC | TTT | GGC | AAG | GGC | ATT | CTC | GAT | CAA | AGC | TGC | GGC | 1031 |
| Thr | Tyr | Val | Phe | Asp | Phe | Gly | Lys | Gly | Ile | Leu | Asp | Gln | Ser | Cys | Gly | |
| | | | 290 | | | | 295 | | | | | 300 | | | | |
| GGT | GTA | TTT | TCA | AAC | AAC | GGC | TCT | TCG | CAA | GTG | CAG | CTG | CGG | GAT | GTA | 1079 |
| Gly | Val | Phe | Ser | Asn | Asn | Gly | Ser | Ser | Gln | Val | Gln | Leu | Arg | Asp | Val | |
| | | 305 | | | | 310 | | | | | 315 | | | | | |
| GTC | TTG | ATG | AAT | GGG | ACA | GTG | GTA | TAC | GAT | TCA | AAC | GGC | GCT | TGG | GAC | 1127 |
| Val | Leu | Met | Asn | Gly | Thr | Val | Val | Tyr | Asp | Ser | Asn | Gly | Ala | Trp | Asp | |
| | 320 | | | | 325 | | | | | 330 | | | | | | |
| AGT | AGT | GCG | CTG | GAG | GAG | TGG | CTC | CAG | CGA | CAG | AAA | AAA | GTT | TCC | ATC | 1175 |
| Ser | Ser | Ala | Leu | Glu | Glu | Trp | Leu | Gln | Arg | Gln | Lys | Lys | Val | Ser | Ile | |
| 335 | | | | 340 | | | | | 345 | | | | | 350 | | |
| GAA | AGA | ATA | TTT | GAA | AAT | ATT | GGG | CCC | AGC | GCC | GTG | TAT | CCG | TCT | ATT | 1223 |
| Glu | Arg | Ile | Phe | Glu | Asn | Ile | Gly | Pro | Ser | Ala | Val | Tyr | Pro | Ser | Ile | |
| | | | | 355 | | | | | 360 | | | | | 365 | | |
| TTG | CCT | GGG | GTC | GTG | ATT | GCG | TCA | CCA | TCG | CAA | ACG | CAT | CCA | GAC | TAC | 1271 |
| Leu | Pro | Gly | Val | Val | Ile | Ala | Ser | Pro | Ser | Gln | Thr | His | Pro | Asp | Tyr | |
| | | | 370 | | | | | 375 | | | | | 380 | | | |
| TTC | TAC | CAA | TGG | ATA | AGG | GAC | AGC | GCG | TTG | ACG | ATA | AAC | AGT | ATT | GTC | 1319 |
| Phe | Tyr | Gln | Trp | Ile | Arg | Asp | Ser | Ala | Leu | Thr | Ile | Asn | Ser | Ile | Val | |
| | | 385 | | | | | 390 | | | | | 395 | | | | |
| TCT | CAT | TCT | GCG | GAC | CCG | GCA | ATA | GAG | ACG | TTA | TTG | CAG | TAC | CTG | AAC | 1367 |
| Ser | His | Ser | Ala | Asp | Pro | Ala | Ile | Glu | Thr | Leu | Leu | Gln | Tyr | Leu | Asn | |
| | 400 | | | | | 405 | | | | | 410 | | | | | |
| GTT | TCA | TTC | CAC | TTG | CAA | AGA | ACC | AAC | AAC | ACA | TTG | GGC | GCT | GGC | ATT | 1415 |
| Val | Ser | Phe | His | Leu | Gln | Arg | Thr | Asn | Asn | Thr | Leu | Gly | Ala | Gly | Ile | |
| 415 | | | | | 420 | | | | | 425 | | | | | 430 | |
| GGT | TAC | ACT | AAC | GAT | ACA | GTG | GCT | TTG | GGA | GAC | CCT | AAG | TGG | AAC | GTC | 1463 |
| Gly | Tyr | Thr | Asn | Asp | Thr | Val | Ala | Leu | Gly | Asp | Pro | Lys | Trp | Asn | Val | |
| | | | | 435 | | | | | 440 | | | | | 445 | | |
| GAC | AAC | ACG | GCT | TTC | ACG | GAA | CCT | TGG | GGT | CGT | CCT | CAA | AAC | GAT | GGC | 1511 |
| Asp | Asn | Thr | Ala | Phe | Thr | Glu | Pro | Trp | Gly | Arg | Pro | Gln | Asn | Asp | Gly | |
| | | | 450 | | | | | 455 | | | | | 460 | | | |
| CCT | GCT | CTT | CGA | AGC | ATT | GCC | ATC | TTA | AAA | ATC | ATC | GAC | TAC | ATC | AAG | 1559 |
| Pro | Ala | Leu | Arg | Ser | Ile | Ala | Ile | Leu | Lys | Ile | Ile | Asp | Tyr | Ile | Lys | |
| | | 465 | | | | | 470 | | | | | 475 | | | | |
| CAA | TCT | GGC | ACT | GAT | CTG | GGG | GCC | AAG | TAC | CCA | TTC | CAG | TCC | ACC | GCA | 1607 |
| Gln | Ser | Gly | Thr | Asp | Leu | Gly | Ala | Lys | Tyr | Pro | Phe | Gln | Ser | Thr | Ala | |
| | 480 | | | | | 485 | | | | | 490 | | | | | |
| GAT | ATC | TTT | GAT | GAT | ATT | GTA | CGT | TGG | TAC | CTG | ATT | AGG | TTC | ATT | ATT | GAC | 1655 |
| Asp | Ile | Phe | Asp | Asp | Ile | Val | Arg | Trp | Tyr | Leu | | Arg | Phe | Ile | Ile | Asp |
| 495 | | | | | 500 | | | | | 505 | | | | | 510 | |
| CAC | TGG | AAT | TCT | TCC | GGA | TTT | GAT | CTA | TGG | GAG | GAA | GTC | AAT | GGC | ATG | 1703 |
| His | Trp | Asn | Ser | Ser | Gly | Phe | Asp | Leu | Trp | Glu | Glu | Val | Asn | Gly | Met | |
| | | | | 515 | | | | | 520 | | | | | 525 | | |
| CAT | TTC | TTT | ACT | TTA | CTG | GTA | CAA | CTG | TCT | GCA | GTG | GAC | AGG | ACG | CTG | 1751 |
| His | Phe | Phe | Thr | Leu | Leu | Val | Gln | Leu | Ser | Ala | Val | Asp | Arg | Thr | Leu | |
| | | | 530 | | | | | 535 | | | | | 540 | | | |

-continued

```
TCG TAT TTT AAC GCC TCA GAA CGG TCG TCT CCC TTT GTT GAA GAA TTG    1799
Ser Tyr Phe Asn Ala Ser Glu Arg Ser Ser Pro Phe Val Glu Glu Leu
        545                 550                 555

CGT CAG ACA CGC CGG GAC ATC TCC AAG TTT TTA GTG GAC CCT GCG AAT    1847
Arg Gln Thr Arg Arg Asp Ile Ser Lys Phe Leu Val Asp Pro Ala Asn
    560                 565                 570

GGG TTT ATC AAC GGC AAG TAC AAT TAT ATT GTT GAG ACA CCC ATG ATT    1895
Gly Phe Ile Asn Gly Lys Tyr Asn Tyr Ile Val Glu Thr Pro Met Ile
575                 580                 585                 590

GCC GAC ACA TTG AGA TCC GGA CTG GAC ATA TCC ACT TTA TTA GCT GCG    1943
Ala Asp Thr Leu Arg Ser Gly Leu Asp Ile Ser Thr Leu Leu Ala Ala
                595                 600                 605

AAC ACC GTC CAC GAT GCG CCA TCT GCT TCC CAT CTT CCG TTC GAT ATC    1991
Asn Thr Val His Asp Ala Pro Ser Ala Ser His Leu Pro Phe Asp Ile
            610                 615                 620

AAT GAC CCT GCC GTC CTG AAC ACG TTG CAC CAT TTG ATG TTG CAC ATG    2039
Asn Asp Pro Ala Val Leu Asn Thr Leu His His Leu Met Leu His Met
        625                 630                 635

CGT TCG ATA TAC CCC ATC AAC GAT AGC TCC AAA AAT GCA ACG GGT ATT    2087
Arg Ser Ile Tyr Pro Ile Asn Asp Ser Ser Lys Asn Ala Thr Gly Ile
    640                 645                 650

GCC CTG GGG CGG TAT CCT GAG GAC GTA TAT GAT GGA TAT GGC GTT GGC    2135
Ala Leu Gly Arg Tyr Pro Glu Asp Val Tyr Asp Gly Tyr Gly Val Gly
655                 660                 665                 670

GAG GGA AAT CCC TGG GTC CTG GCC ACG TGT GCC GCT TCA ACA ACG CTT    2183
Glu Gly Asn Pro Trp Val Leu Ala Thr Cys Ala Ala Ser Thr Thr Leu
                675                 680                 685

TAT CAG CTC ATT TAC AGA CAC ATC TCT GAG CAG CAT GAC TTG GTT GTC    2231
Tyr Gln Leu Ile Tyr Arg His Ile Ser Glu Gln His Asp Leu Val Val
            690                 695                 700

CCA ATG AAC AAC GAT TGT TCG AAC GCA TTT TGG AGC GAG CTG GTA TTC    2279
Pro Met Asn Asn Asp Cys Ser Asn Ala Phe Trp Ser Glu Leu Val Phe
        705                 710                 715

TCC AAC CTC ACG ACT TTG GGA AAT GAC GAA GGC TAT TTG ATT TTG GAG    2327
Ser Asn Leu Thr Thr Leu Gly Asn Asp Glu Gly Tyr Leu Ile Leu Glu
    720                 725                 730

TTC AAT ACA CCT GCC TTC AAT CAA ACC ATA CAA AAA ATC TTC CAA CTA    2375
Phe Asn Thr Pro Ala Phe Asn Gln Thr Ile Gln Lys Ile Phe Gln Leu
735                 740                 745                 750

GCT GAT TCA TTC TTG GTC AAG CTG AAA GCC CAC GTG GGA ACA GAC GGG    2423
Ala Asp Ser Phe Leu Val Lys Leu Lys Ala His Val Gly Thr Asp Gly
                755                 760                 765

GAA CTA AGT GAA CAA TTT AAC AAA TAC ACA GGG TTT ATG CAG GGT GCC    2471
Glu Leu Ser Glu Gln Phe Asn Lys Tyr Thr Gly Phe Met Gln Gly Ala
            770                 775                 780

CAA CAC CTT ACC TGG TCC TAT ACT TCA TTC TGG GAT GCC TAT CAA ATA    2519
Gln His Leu Thr Trp Ser Tyr Thr Ser Phe Trp Asp Ala Tyr Gln Ile
        785                 790                 795

AGA CAA GAA GTT TTA CAG AGT TTG TAGACAAAAA AAAATAAAAG AAAAGCGAGA   2573
Arg Gln Glu Val Leu Gln Ser Leu
    800                 805

AGTATACACA AGTGTATTTC CTAGATATTT ACATCAAATA TATATATATA TACTTATTTA  2633

CAAAACTCTG ATATTATAAA TTAATTAGAT AACTATGTCG GAACGTCCAG CCCAACCACG  2693

TTTGCAGTTC TTTTCACTTT CTCATCCTGT GTCAACTTGT TGCCGGATTG TATCTGTCGA  2753

C                                                                  2754
```

( 2 ) INFORMATION FOR SEQ ID NO:11:

( i ) SEQUENCE CHARACTERISTICS:

(A) LENGTH: 806 amino acids
(B) TYPE: amino acid
(D) TOPOLOGY: linear (ii) MOLECULE TYPE: protein (xi) SEQUENCE DESCRIPTION: SEQ ID NO:11:

```
Met Gln Arg Pro Phe Leu Leu Ala Tyr Leu Val Leu Ser Leu Leu Phe
 1               5                  10                  15
Asn Ser Ala Leu Gly Phe Pro Thr Ala Leu Val Pro Arg Gly Ser Ser
            20                  25                  30
Ser Ser Asn Ile Thr Ser Ser Gly Pro Ser Ser Thr Pro Phe Ser Ser
                35                  40                  45
Ala Thr Glu Ser Phe Ser Thr Gly Thr Thr Val Thr Pro Ser Ser Ser
        50                  55                  60
Lys Tyr Pro Gly Ser Lys Thr Glu Thr Ser Val Ser Ser Thr Thr Glu
 65                  70                  75                  80
Thr Thr Ile Val Pro Thr Thr Thr Thr Thr Ser Val Ile Thr Pro Ser
                 85                  90                  95
Thr Thr Thr Ile Thr Thr Thr Val Cys Ser Thr Gly Thr Asn Ser Ala
            100                 105                 110
Gly Glu Thr Thr Ser Gly Cys Ser Pro Lys Thr Ile Thr Thr Thr Val
            115                 120                 125
Pro Cys Ser Thr Ser Pro Ser Glu Thr Ala Ser Glu Ser Thr Thr Thr
    130                 135                 140
Ser Pro Thr Thr Pro Val Thr Thr Val Val Ala Thr Thr Val Val Thr
145                 150                 155                 160
Thr Glu Tyr Ser Thr Ser Thr Lys Gln Gly Gly Glu Ile Thr Thr Thr
                165                 170                 175
Phe Val Thr Lys Asn Ser Pro Thr Thr Tyr Leu Thr Thr Ile Ala Pro
            180                 185                 190
Thr Ser Ser Val Thr Thr Val Thr Asn Phe Thr Pro Thr Thr Ile Thr
        195                 200                 205
Thr Thr Val Cys Ser Thr Gly Thr Asn Ser Ala Gly Glu Thr Thr Ser
    210                 215                 220
Gly Cys Ser Pro Lys Thr Val Thr Thr Thr Val Leu Cys Ser Thr Gly
225                 230                 235                 240
Thr Gly Glu Tyr Thr Thr Glu Ala Thr Ala Pro Val Thr Thr Ala Val
                245                 250                 255
Thr Thr Thr Val Val Thr Thr Glu Ser Ser Thr Gly Thr Asn Ser Val
            260                 265                 270
Gly Lys Thr Thr Thr Ser Tyr Thr Thr Lys Ser Val Pro Thr Thr Tyr
        275                 280                 285
Val Phe Asp Phe Gly Lys Gly Ile Leu Asp Gln Ser Cys Gly Gly Val
    290                 295                 300
Phe Ser Asn Asn Gly Ser Ser Gln Val Gln Leu Arg Asp Val Val Leu
305                 310                 315                 320
Met Asn Gly Thr Val Val Tyr Asp Ser Asn Gly Ala Trp Asp Ser Ser
                325                 330                 335
Ala Leu Glu Glu Trp Leu Gln Arg Gln Lys Lys Val Ser Ile Glu Arg
            340                 345                 350
Ile Phe Glu Asn Ile Gly Pro Ser Ala Val Tyr Pro Ser Ile Leu Pro
        355                 360                 365
Gly Val Val Ile Ala Ser Pro Ser Gln Thr His Pro Asp Tyr Phe Tyr
    370                 375                 380
```

```
Gln Trp Ile Arg Asp Ser Ala Leu Thr Ile Asn Ser Ile Val Ser His
385                 390                 395                 400

Ser Ala Asp Pro Ala Ile Glu Thr Leu Leu Gln Tyr Leu Asn Val Ser
                405                 410                 415

Phe His Leu Gln Arg Thr Asn Asn Thr Leu Gly Ala Gly Ile Gly Tyr
            420                 425                 430

Thr Asn Asp Thr Val Ala Leu Gly Asp Pro Lys Trp Asn Val Asp Asn
        435                 440                 445

Thr Ala Phe Thr Glu Pro Trp Gly Arg Pro Gln Asn Asp Gly Pro Ala
    450                 455                 460

Leu Arg Ser Ile Ala Ile Leu Lys Ile Ile Asp Tyr Ile Lys Gln Ser
465                 470                 475                 480

Gly Thr Asp Leu Gly Ala Lys Tyr Pro Phe Gln Ser Thr Ala Asp Ile
                485                 490                 495

Phe Asp Asp Ile Val Arg Trp Tyr Leu Arg Phe Ile Ile Asp His Trp
            500                 505                 510

Asn Ser Ser Gly Phe Asp Leu Trp Glu Glu Val Asn Gly Met His Phe
        515                 520                 525

Phe Thr Leu Leu Val Gln Leu Ser Ala Val Asp Arg Thr Leu Ser Tyr
    530                 535                 540

Phe Asn Ala Ser Glu Arg Ser Ser Pro Phe Val Glu Glu Leu Arg Gln
545                 550                 555                 560

Thr Arg Arg Asp Ile Ser Lys Phe Leu Val Asp Pro Ala Asn Gly Phe
                565                 570                 575

Ile Asn Gly Lys Tyr Asn Tyr Ile Val Glu Thr Pro Met Ile Ala Asp
            580                 585                 590

Thr Leu Arg Ser Gly Leu Asp Ile Ser Thr Leu Leu Ala Ala Asn Thr
        595                 600                 605

Val His Asp Ala Pro Ser Ala Ser His Leu Pro Phe Asp Ile Asn Asp
    610                 615                 620

Pro Ala Val Leu Asn Thr Leu His His Leu Met Leu His Met Arg Ser
625                 630                 635                 640

Ile Tyr Pro Ile Asn Asp Ser Ser Lys Asn Ala Thr Gly Ile Ala Leu
                645                 650                 655

Gly Arg Tyr Pro Glu Asp Val Tyr Asp Gly Tyr Gly Val Gly Glu Gly
            660                 665                 670

Asn Pro Trp Val Leu Ala Thr Cys Ala Ala Ser Thr Thr Leu Tyr Gln
        675                 680                 685

Leu Ile Tyr Arg His Ile Ser Glu Gln His Asp Leu Val Val Pro Met
    690                 695                 700

Asn Asn Asp Cys Ser Asn Ala Phe Trp Ser Glu Leu Val Phe Ser Asn
705                 710                 715                 720

Leu Thr Thr Leu Gly Asn Asp Glu Gly Tyr Leu Ile Leu Glu Phe Asn
                725                 730                 735

Thr Pro Ala Phe Asn Gln Thr Ile Gln Lys Ile Phe Gln Leu Ala Asp
            740                 745                 750

Ser Phe Leu Val Lys Leu Lys Ala His Val Gly Thr Asp Gly Glu Leu
        755                 760                 765

Ser Glu Gln Phe Asn Lys Tyr Thr Gly Phe Met Gln Gly Ala Gln His
    770                 775                 780

Leu Thr Trp Ser Tyr Thr Ser Phe Trp Asp Ala Tyr Gln Ile Arg Gln
785                 790                 795                 800

Glu Val Leu Gln Ser Leu
                805
```

( 2 ) INFORMATION FOR SEQ ID NO:12:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: -
        ( B ) LOCATION: 1..54
        ( D ) OTHER INFORMATION: /label=linker
            / note= "linker used to create pAYE274"

( x i ) SEQUENCE DESCRIPTION: SEQ ID NO:12:

```
ACGGCCCCCC CGGCCACAAA CACAAATATT GATAATATAA AGATGAAGTG GGTA          54
```

( 2 ) INFORMATION FOR SEQ ID NO:13:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: -
        ( B ) LOCATION: 1..60
        ( D ) OTHER INFORMATION: /label=Linker
            / note= "Synthetic oligonucleotide linker used to
            construct pAYE309"

( x i ) SEQUENCE DESCRIPTION: SEQ ID NO:13:

```
AGCTTTATTT CCCTTCTTTT TCTCTTTAGC TCGGCTTATT CCAGGAGCTT GGATAAAAGA   60
```

( 2 ) INFORMATION FOR SEQ ID NO:14:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: misc_feature
        ( B ) LOCATION: 1..19
        ( D ) OTHER INFORMATION: /function="Linker"
            / note= "Linker used in construction of pDXL200.
            Contains SfiI, BglII and HindIII sites."

( x i ) SEQUENCE DESCRIPTION: SEQ ID NO:14:

```
GTACGGCCCC CCCGGCCAGA TCTAAGCTT                                      29
```

( 2 ) INFORMATION FOR SEQ ID NO:15:

( i ) SEQUENCE CHARACTERISTICS:
        ( A ) LENGTH: 58 base pairs
        ( B ) TYPE: nucleic acid

```
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: misc_feature
        ( B ) LOCATION: 1..58
        ( D ) OTHER INFORMATION: /function="Linker"
              / note= "Complementary strand to SEQ ID No:12"

( x i ) SEQUENCE DESCRIPTION: SEQ ID NO:15:

AGCTTACCCA  CTTCATCTTT  ATATTATCAA  TATTTGTGTT  TGTGGCCGGG  GGGGCCGT        58

( 2 ) INFORMATION FOR SEQ ID NO:16:

( i ) SEQUENCE CHARACTERISTICS:
        ( A ) LENGTH: 56 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: misc_feature
        ( B ) LOCATION: 1..56
        ( D ) OTHER INFORMATION: /function="Linker"
              / note= "Complementary strand to SEQ ID No:13"

( x i ) SEQUENCE DESCRIPTION: SEQ ID NO:16:

TCTTTTATCC  AAGCTCCTGG  AATAAGCCGA  GCTAAAGAGA  AAAAGAAGGG  AAATAA        56

( 2 ) INFORMATION FOR SEQ ID NO:17:

( i ) SEQUENCE CHARACTERISTICS:
        ( A ) LENGTH: 29 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: misc_feature
        ( B ) LOCATION: 1..29
        ( D ) OTHER INFORMATION: /function="Linker"
              / note= "Complementary strand to SEQ ID No:14"

( x i ) SEQUENCE DESCRIPTION: SEQ ID NO:17:

AAGCTTAGAT  CTGGCCGGGG  GGGCCGTAC        29
```